(12) United States Patent
Campbell et al.

(10) Patent No.: US 11,892,400 B1
(45) Date of Patent: Feb. 6, 2024

(54) REFLECTIVE DEPTH INTERROGATION FOR ANALYTE MEASUREMENT IN LIQUIDS

(71) Applicant: Airware, Inc., Newbury Park, CA (US)

(72) Inventors: Thomas G Campbell, Newbury Park, CA (US); Jacob Y Wong, Goleta, CA (US)

(73) Assignee: AIRWARE, INC, Newbury Park, CA (US)

( * ) Notice: Subject to any disclaimer, the term of this patent is extended or adjusted under 35 U.S.C. 154(b) by 0 days.

(21) Appl. No.: 18/238,300

(22) Filed: Aug. 25, 2023

Related U.S. Application Data

(63) Continuation-in-part of application No. 18/114,414, filed on Feb. 27, 2023, now Pat. No. 11,747,259, which is a continuation-in-part of application No. 17/227,789, filed on Apr. 12, 2021, now Pat. No. 11,604,138, which is a continuation of application No. 17/073,297, filed on Oct. 17, 2020, now Pat. No. 10,976,243, which is a continuation-in-part of application No. 16/600,466, filed on Oct. 12, 2019, now Pat. No. 10,983,046, which is a continuation-in-part of application No. 16/359,350, filed on Mar. 20, 2019, now Pat. No. 10,473,586, (Continued)

(51) Int. Cl.
| | |
|---|---|
| *G01N 33/487* | (2006.01) |
| *G01N 21/31* | (2006.01) |
| *G01N 21/35* | (2014.01) |
| *A61B 5/145* | (2006.01) |
| *A61B 5/00* | (2006.01) |
| *G01N 21/3577* | (2014.01) |
| *A61B 5/1455* | (2006.01) |
| *G01N 21/21* | (2006.01) |
| *G01N 33/49* | (2006.01) |

(52) U.S. Cl.
CPC ....... *G01N 21/3151* (2013.01); *A61B 5/0075* (2013.01); *A61B 5/1451* (2013.01); *A61B 5/1455* (2013.01); *A61B 5/14532* (2013.01); *G01N 21/3577* (2013.01); *G01N 33/487* (2013.01); *A61B 5/0062* (2013.01); *A61B 2562/0238* (2013.01); *G01N 21/21* (2013.01); *G01N 33/49* (2013.01); *G01N 2021/3148* (2013.01); *G01N 2201/10* (2013.01)

(58) Field of Classification Search
CPC ... A61B 5/0062; A61B 5/0075; A61B 5/1451; A61B 5/14532; A61B 5/1455; A61B 2562/0238; G01N 21/21; G01N 21/3151; G01N 21/3577; G01N 33/487; G01N 33/49; G01N 2021/3148; G01N 2201/10
See application file for complete search history.

(56) References Cited

U.S. PATENT DOCUMENTS 6,509,567 B2 * 1/2003 Boudet ............... G01N 21/314
250/575

* cited by examiner

*Primary Examiner* — Mark R Gaworecki
(74) *Attorney, Agent, or Firm* — Roy L Anderson

(57) ABSTRACT

An absorption spectroscopy process uses a single radiation beam with two or more pulsed beams (including at least a signal beam and a reference beam) that are passed into a liquid sample to a variable effective depth and then reflected out of the liquid sample where it is detected and processed to obtain a value over a preselected time. As values are determined for multiple effective depths, a sampling dataset is obtained which is used to calculate a concentration level of a targeted particle in the liquid sample by use of calibration dataset obtained from use of known samples.

20 Claims, 31 Drawing Sheets

Shallow focus

Deep focus

Related U.S. Application Data which is a continuation-in-part of application No. 16/056,531, filed on Aug. 7, 2018, now Pat. No. 10,241,044, which is a continuation-in-part of application No. 15/785,829, filed on Oct. 17, 2017, now Pat. No. 10,041,881, which is a continuation-in-part of application No. 15/644,775, filed on Jul. 8, 2017, now Pat. No. 9,823,185, which is a continuation-in-part of application No. 15/594,418, filed on May 12, 2017, now Pat. No. 9,726,601, which is a continuation-in-part of application No. 15/444,136, filed on Feb. 27, 2017, now Pat. No. 9,678,000, which is a continuation-in-part of application No. 15/358,873, filed on Nov. 22, 2016, now Pat. No. 9,606,053.

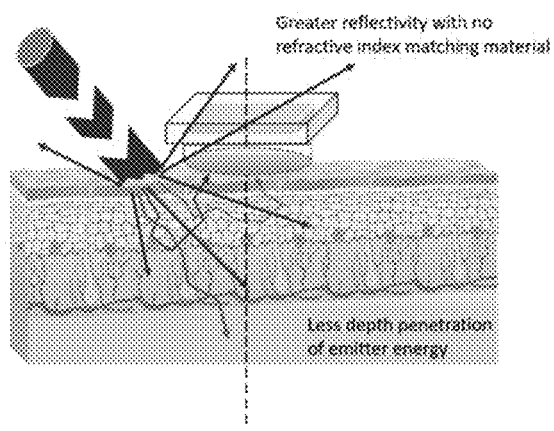
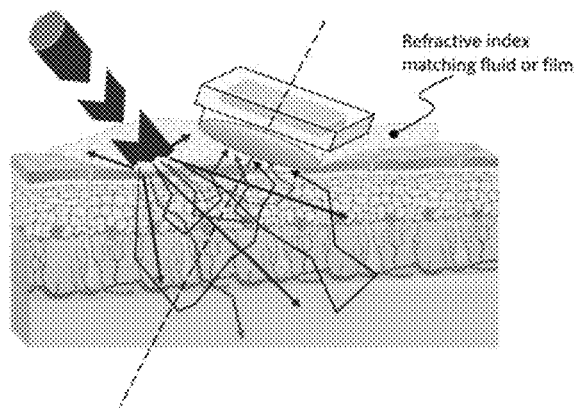
FIG. 3A                    FIG. 3B (PRIOR ART)

FIG. 12A
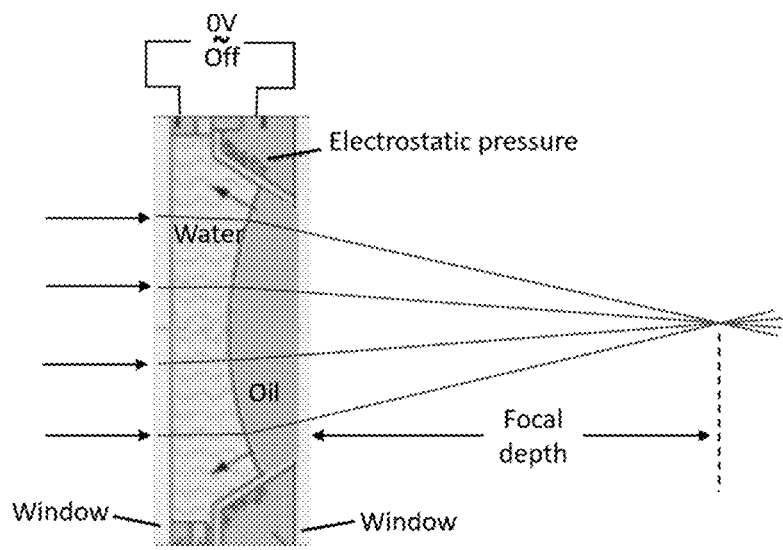
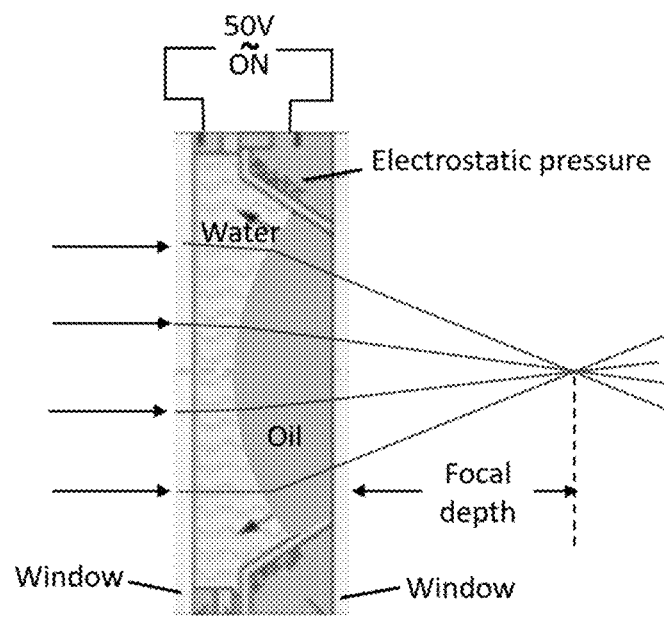
FIG. 12B

FIG. 13A
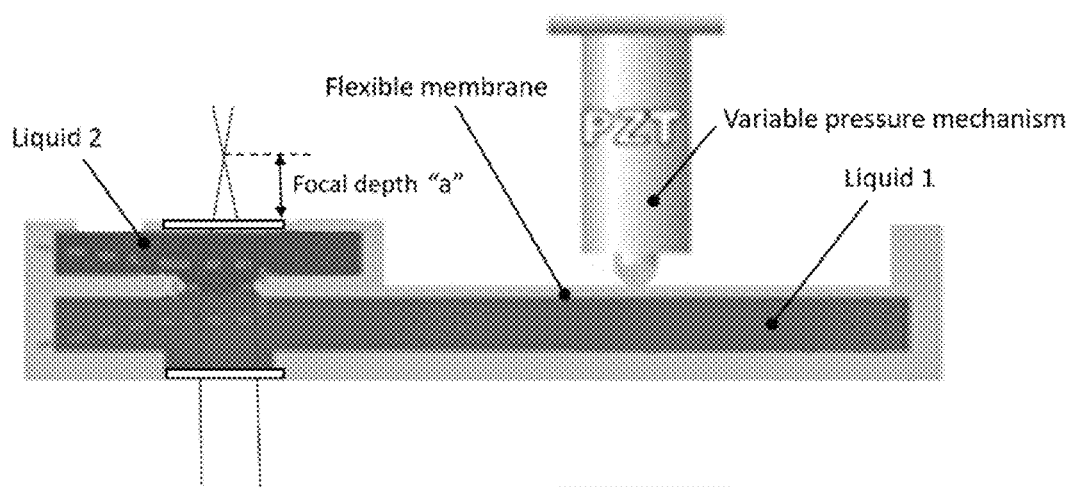
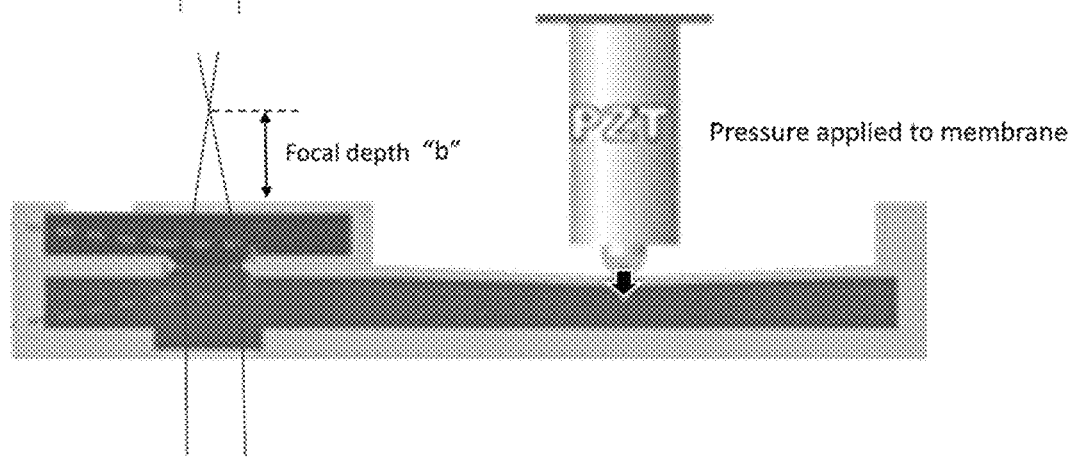
FIG. 13B

Fig. XX

REFLECTIVE DEPTH INTERROGATION FOR ANALYTE MEASUREMENT IN LIQUIDS

CROSS-REFERENCE TO RELATED APPLICATIONS

The present invention is a continuation-in-part application of U.S. Ser. No. 18/114,414, filed Feb. 27, 2023, to issue Sep. 5, 2023 as U.S. Pat. No. 11,747,259, which is a continuation-in-part of U.S. Ser. No. 17/227,789, filed Apr. 12, 2021, issued Mar. 14, 2023 as U.S. Pat. No. 11,604,138, which is a continuation application of U.S. Ser. No. 17/073,297, filed Oct. 17, 2020, issued on Apr. 13, 2021 as U.S. Pat. No. 10,976,242, which is a continuation-in-part application of U.S. Ser. No. 16/600,466, filed Oct. 12, 2019, issued on Apr. 20, 2021 as U.S. Pat. No. 10,983,046, which is a continuation of U.S. Ser. No. 16/359,350, filed Mar. 20, 2019, issued on Nov. 12, 2019 as U.S. Pat. No. 10,473,586, which is a continuation-in-part application of U.S. Ser. No. 16/056,531, filed Aug. 7, 2018, issued on Mar. 26, 2029 as U.S. Pat. No. 10,241,044, which is a continuation-in-part of U.S. Ser. No. 15/785,829 filed Oct. 17, 2017, issued Aug. 7, 2018 as U.S. Pat. No. 10,041,881, which is a continuation-in-part of U.S. Ser. No. 15/644,775 filed Jul. 8, 2017, issued Nov. 21, 2017 as U.S. Pat. No. 9,823,185, which is a continuation in part of U.S. Ser. No. 15/594,418 filed May 12, 2017, issued Aug. 8, 2017 as U.S. Pat. No. 9,726,601, which is a continuation-in-part application of U.S. Ser. No. 15/444,136 filed Feb. 27, 2017, issued Jun. 13, 2017 as U.S. Pat. No. 9,678,000, which is a continuation-in-part application of U.S. Ser. No. 15/358,873, filed Nov. 22, 2016, issued Mar. 28, 2017 as U.S. Pat. No. 9,606,053, the disclosures of all of which are specifically incorporated herein by reference.

FIELD OF THE INVENTION

The present invention relates to liquid absorption spectroscopy.

BACKGROUND OF THE INVENTION

The present invention seeks to advance the field which its inventors have pioneered, especially for use in detecting target molecules, such as glucose, in liquid samples, such as in vitro mammalian tissues.

More particularly, the present invention seeks to enhance precision measurements when a reflective technique, rather than a transmissive technique, is used to interrogate a water sample, such as human skin. In this new technique, rather than using a constant volume interrogation ("CVI"), as has been previously used with the transmissive technique, a quasi-volume is established for each measurement by use of multiple effective focal depths of light energy and calibration uses a sampling dataset and a calibration dataset.

This and further objects and advantages will be apparent to those skilled in the art in connection with the figures and the detailed description of the invention set forth below.

SUMMARY OF THE INVENTION

The present invention is generally directed to absorption spectroscopy processes which use a single radiation beam with two or more pulsed beams (including at least a signal beam and a reference beam) that are passed into a liquid sample to a variable effective depth and then reflected out of the liquid sample where it is detected and processed to obtain a value over a preselected time. As values are determined for multiple effective depths, a sampling dataset is obtained which is used to calculate a concentration level of a targeted particle in the liquid sample with an absorption band in the signal beam, the reference beam not being coincident with such absorption band. The variable effective depth can be achieved by changing the power level of the single radiation beam or by different focusing depths. The calibration dataset can be obtained from use of the absorption spectroscopy process on samples of known concentration, which can also take into account multiple human conditions and variable identical pathlengths.

Accordingly, the object of the present invention is to provide an improved system and process for detection of molecules in a liquid medium which uses a reflective interrogation technique.

This and further objects and advantages will be apparent to those skilled in the art in connection with the figures and the detailed description of the invention set forth below.

BRIEF DESCRIPTION OF THE DRAWINGS

FIGS. 3A and 3B illustrate an emitter and detector angle with no refractive index matching material and with a refractive index matching fluid or film, respectively.

FIGS. 12A and 12B illustrate a variable focus technology in which voltage is applied to creating electro-static pressure to deform one or more surfaces.

FIGS. 13A and 13B illustrate a variable focus technology in which a variable mechanical pressure is applied to deform one or more surfaces.

For FIGS. 20 C and D, the emitter axis is non-perpendicular to the liquid matrix and the detector system is also position in a non-perpendicular arrangement to the liquid matrix. With the dotted line indicating the lowered lens position, it is apparent that having the detector system slightly further away from the raised and lowered single lens will allow less constricted movement of the skin as various focal depth interrogations are processed for analyte concentration scanning of the skin.

Figure 21:
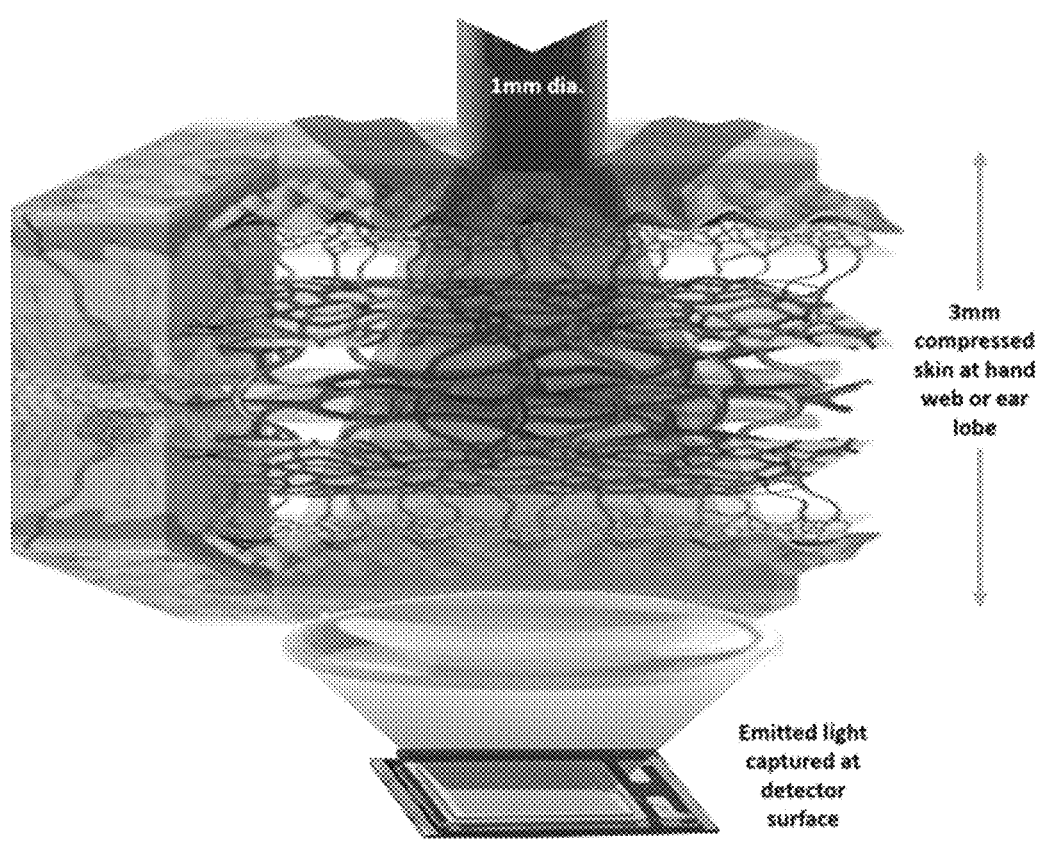

FIG. 21 portrays an optical transmissive sensing configuration with a controlled interrogation volume for comparison to a reflective sensing configuration.

Figure 22A:
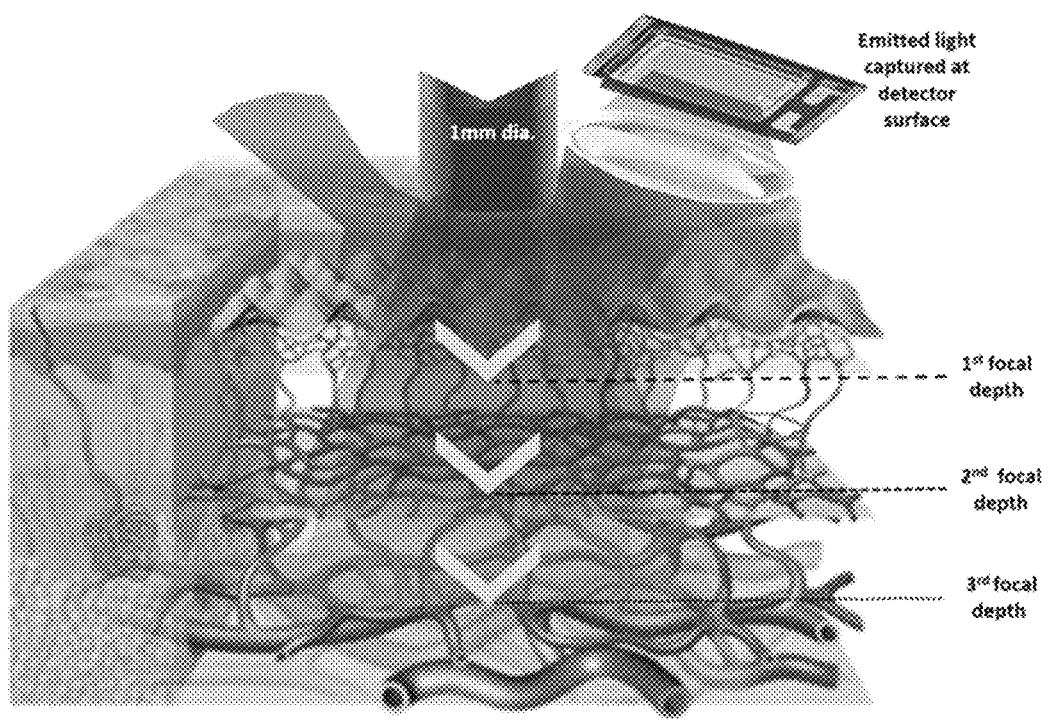
Figure 22B:
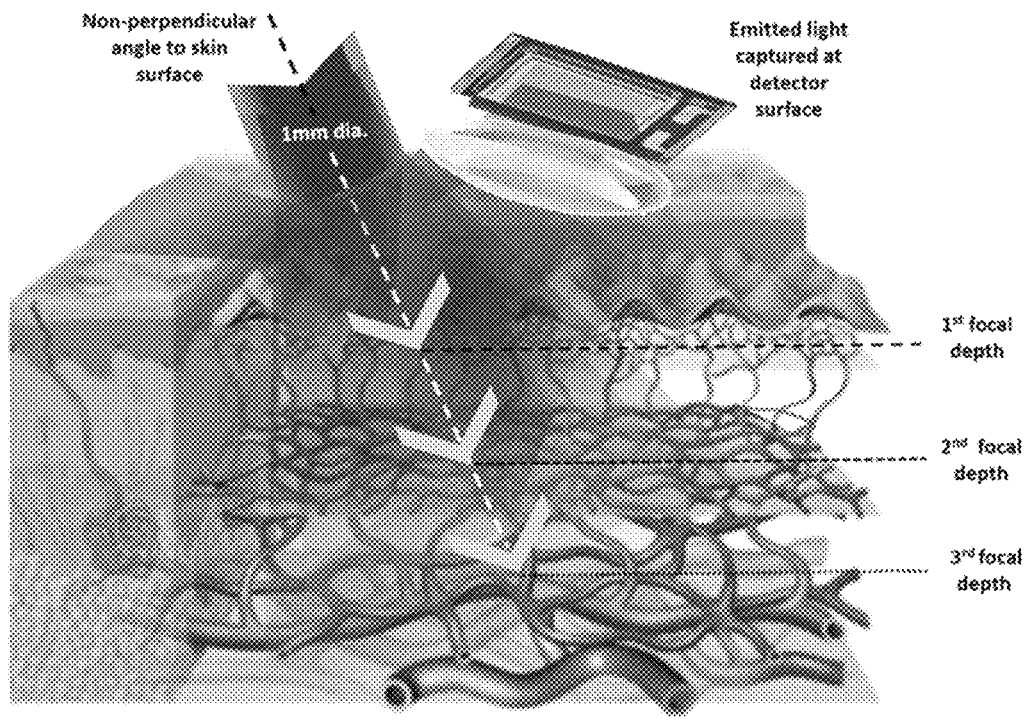

FIGS. 22A and 22B represent reflective sensing configurations with a comparison of focal depths of the interrogating emitter light energy into a liquid matrix with a perpendicular emitter and an emitter off a perpendicular axis, respectively.

Figure 23:
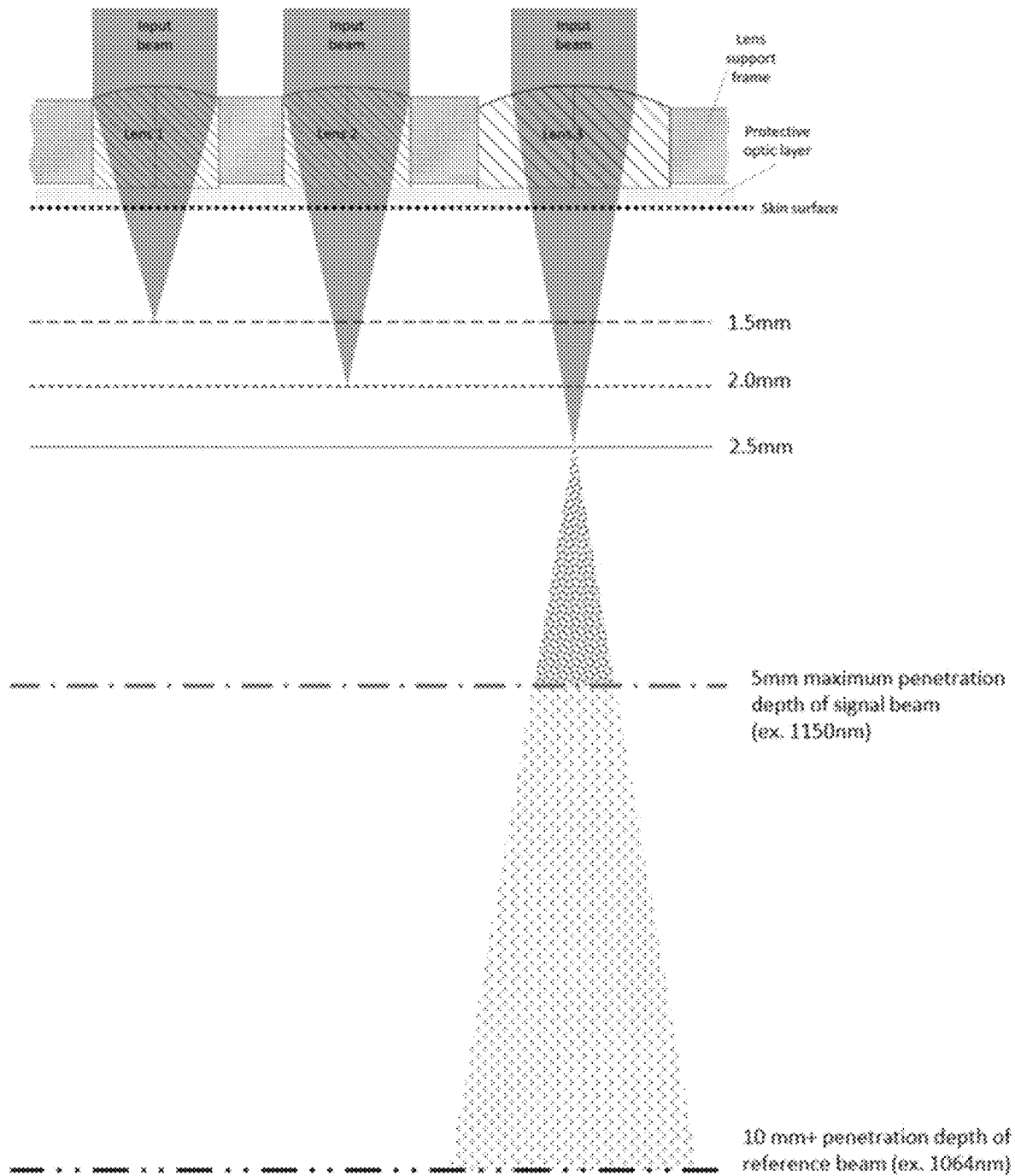

FIG. 23 helps to visualize how absorptions between different wavelengths relate to their penetration depths into a liquid matrix.

Figure 24:
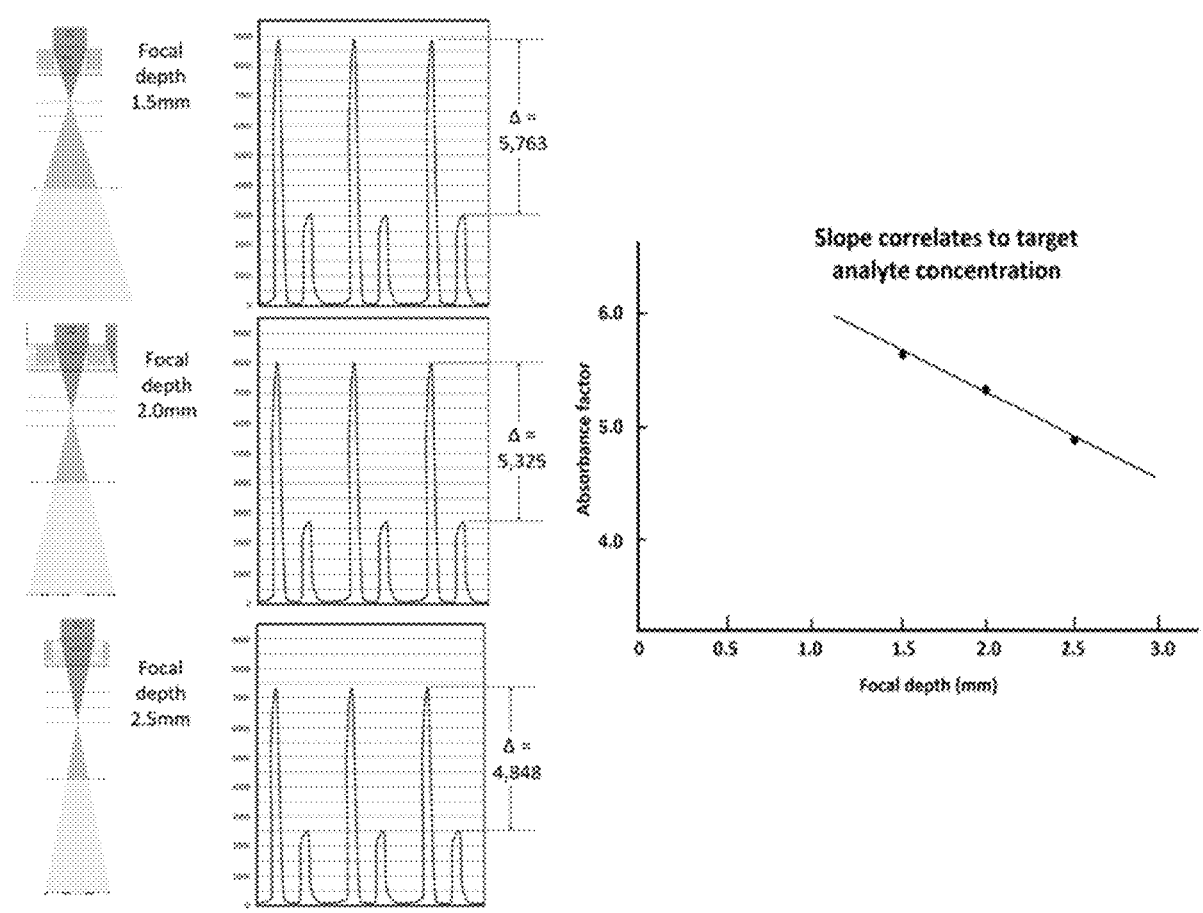

FIG. 24 represents data collected over three focal depths of reference and target analyte sequentially pulsed lasers. Absorbance values are plotted against Focal Depth and slope of the line through the points correlates to a known concentration value for a matching liquid matrix.

Figure 25A:
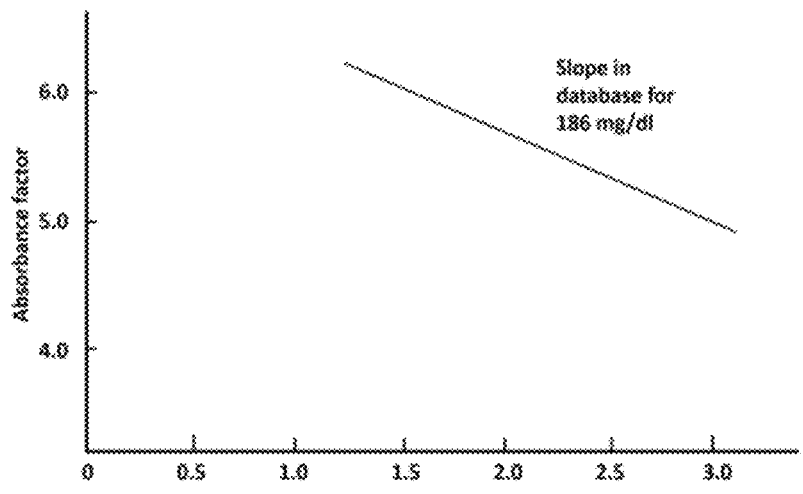
Figure 25B:
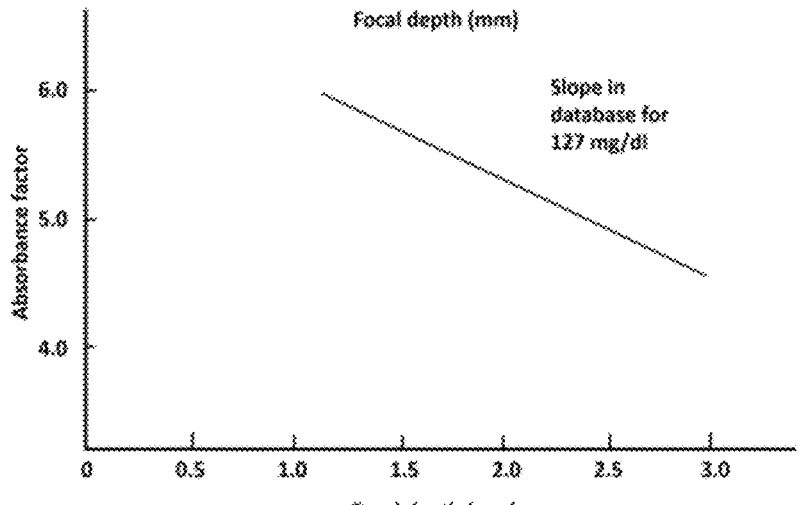
Figure 25C:
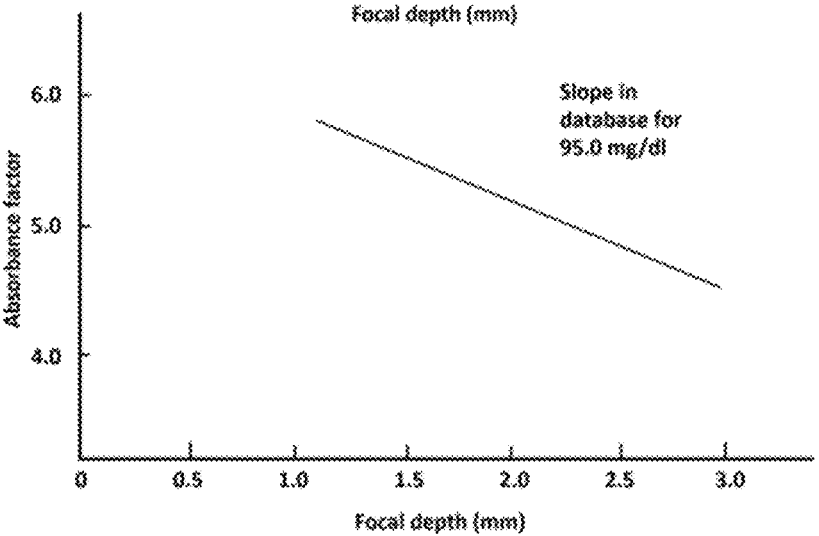

FIGS. 25A-C show a subset of developed databases of known dosed values for particular liquid matrices matching to the liquid matrix under interrogation.

Figure 26A:
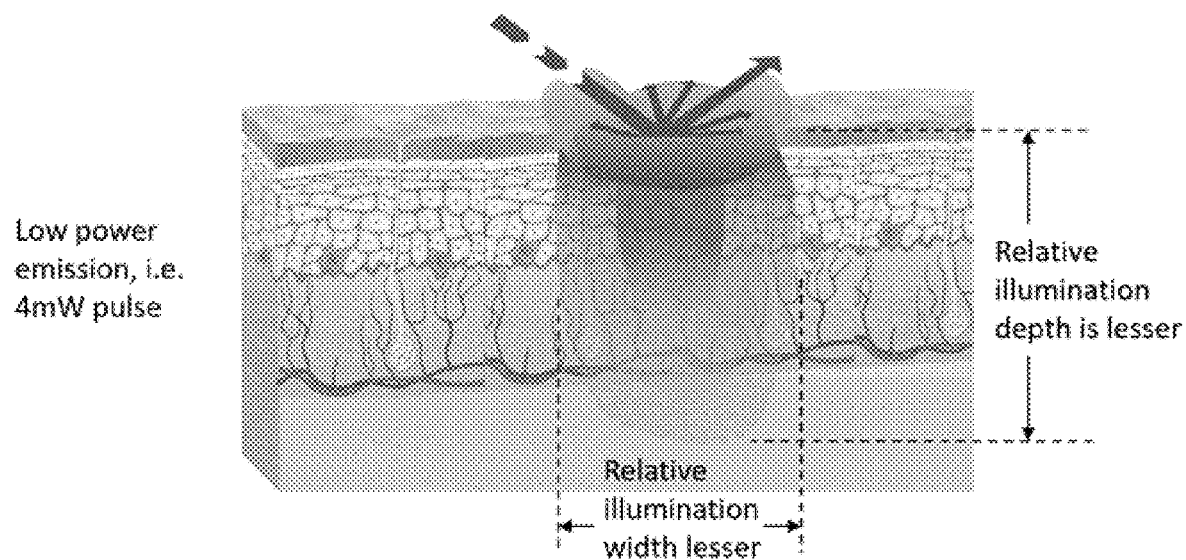
Figure 26B:
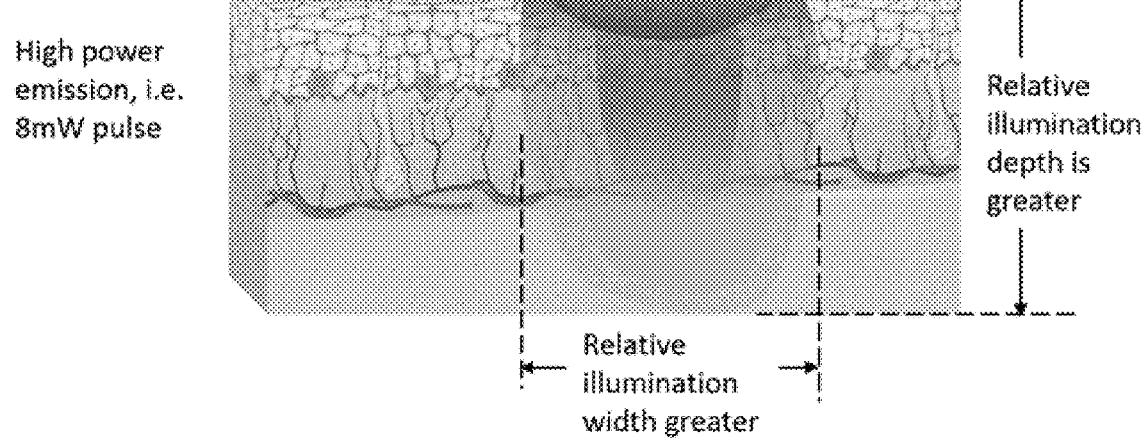

FIGS. 26A and 26B portray variation in penetration depth and with of pattern of scattering, absorption, extinction, and transmission with variation of the input beam pulse power.

Figure 27:
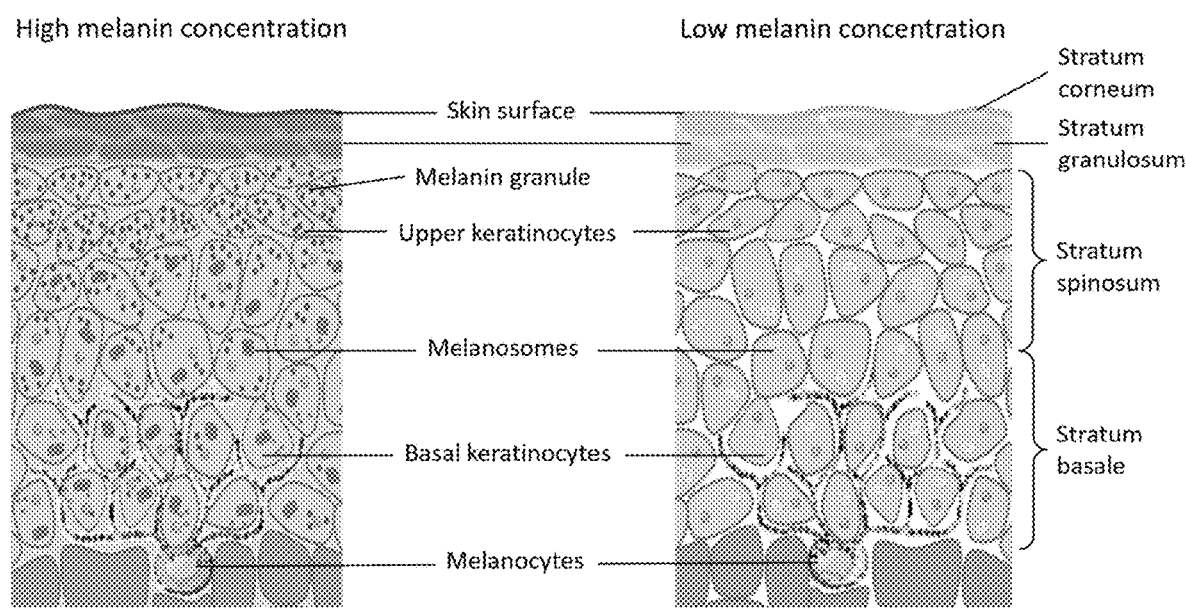

FIG. 27 is a graphic presentation of high and low melanin content in the uppermost layers of human skin.

Figure 28:
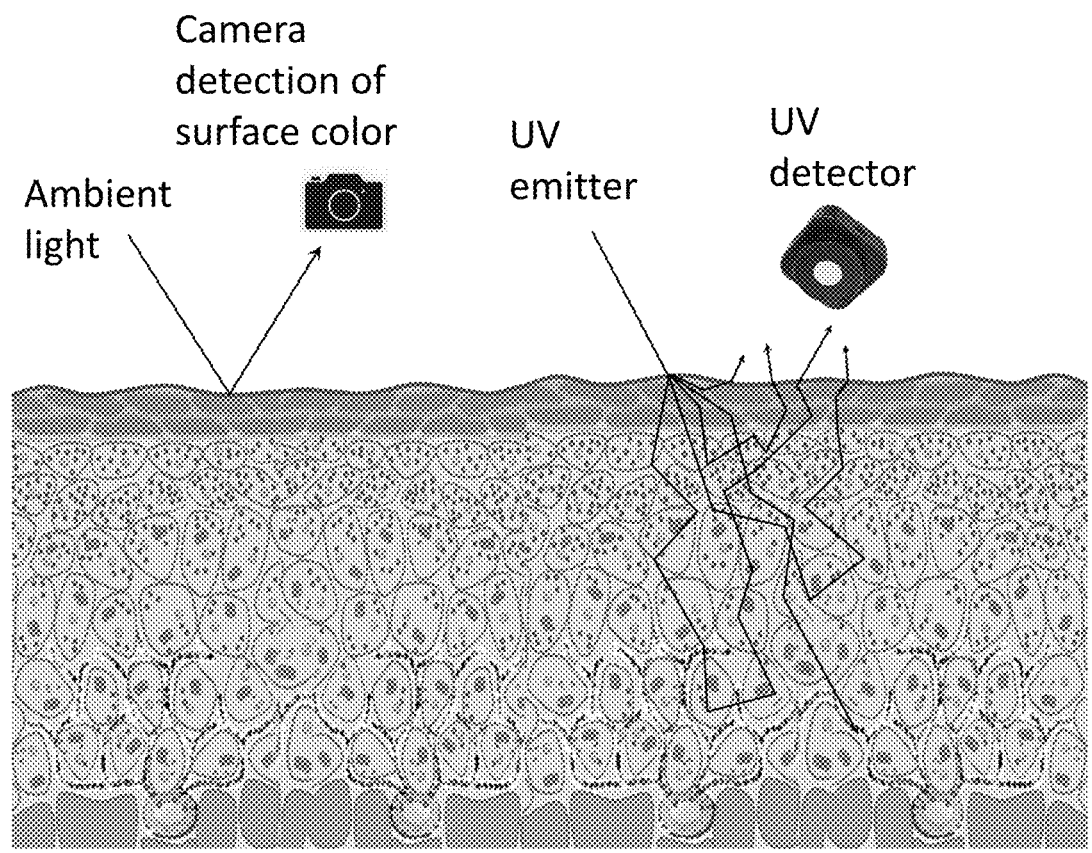

FIG. 28 illustrates two techniques for determining a melanin content of human skin. One through use of a color camera capturing ambient surface reflected light and one that employs both a UV emitter and a UV detector.

Figure 29:
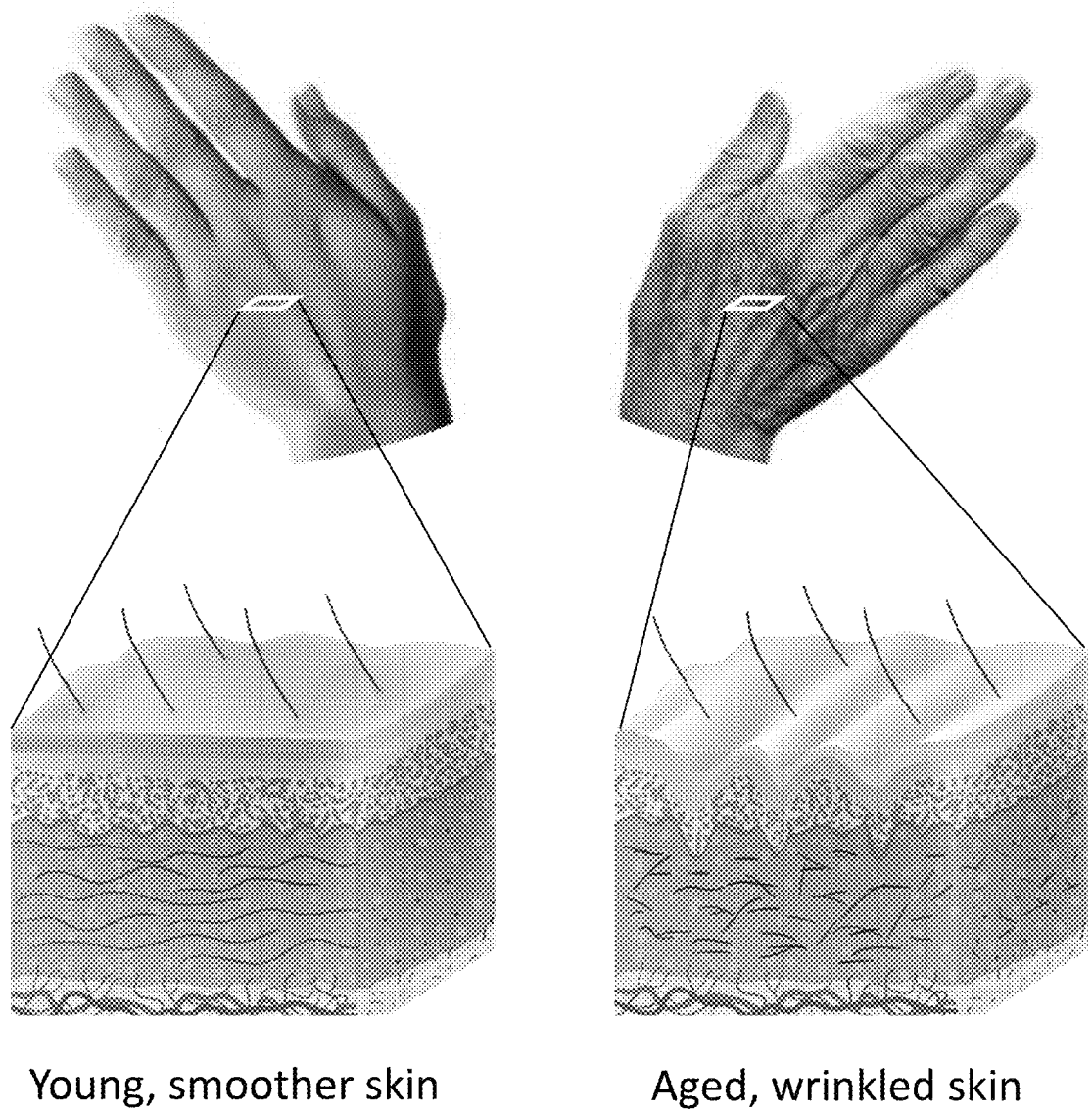

FIG. 29 shows two hands, one of young individual with smooth skin and one of an aged individual exhibiting wrinkles. For each skin type, a cross sectional view highlights differences in surface condition.

Figure 30:
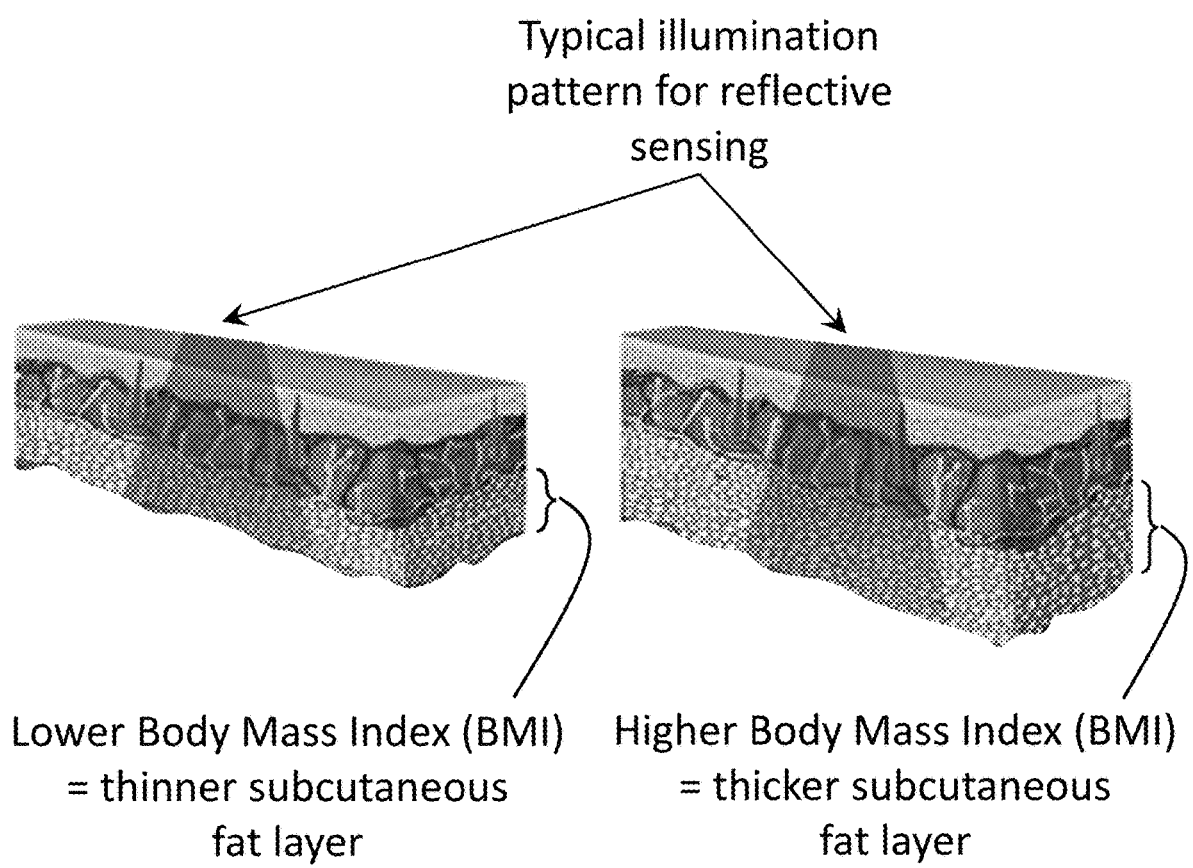

FIG. 30 reveals differences in adipose fat layers between low and high Body Mass Index (BMI) conditions.

Figure 31:
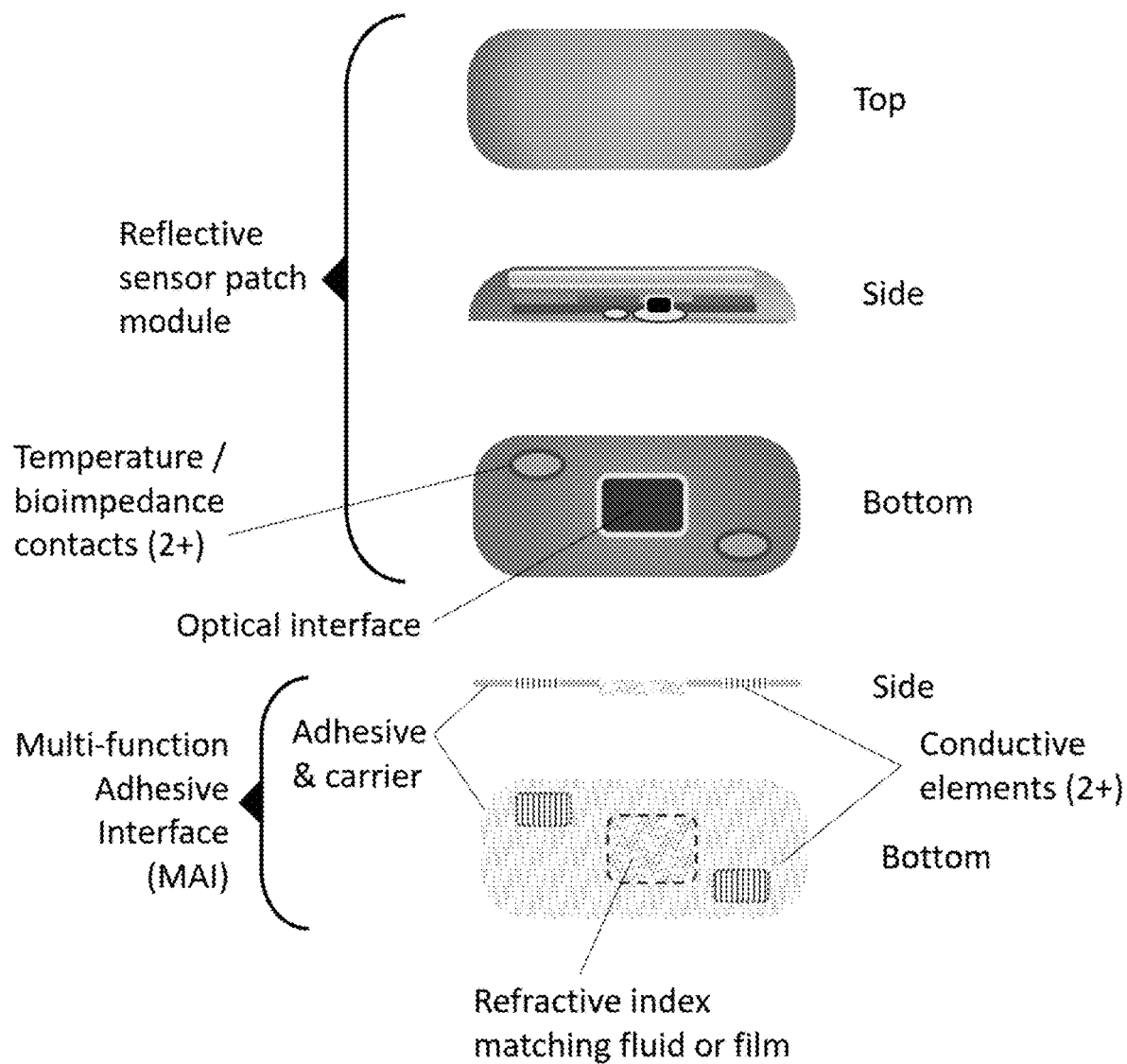

FIG. 31 represents an embodiment of a Reflective Sensor Patch module and the accompanying Multi-function Adhesive Interface (MAI).

DETAILED DESCRIPTION OF THE INVENTION

The present invention describes an improvement to the work set forth earlier in the family of patents cross-referenced above, and familiarity with this body of work is assumed. For example, U.S. Pat. No. 11,604,138 describes an absorption spectroscopy process for quantifying a concentration of a targeted molecule in a liquid sample, U.S. Pat. No. 9,726,601 describes the addition of an interference source for use with interfering molecules while U.S. Pat. No. 9,823,185 describes the use of reflection from a spot of a liquid sampling matrix.

Use of inventions set forth in our earlier body of work has led to achieving clinical accuracy in sensing an analyte in skin with transmissive optical sensing. Efforts have been focused upon a Tissue Optical Window where the specific range of wavelengths have relatively strong depth penetration in human tissue to interact with biological structures effectively. Generally, this optical window lies within the near-infrared (NIR) spectrum, ranging from 650 nm to 1350 nm.

Having tailored the chosen wavelengths within the Tissue Optical Window range, there is ultimately adequate signal received at the detector for precise and repeatable measurement. Looking to expand on the physical range of applications for optical analyte sensing, the present disclosure seeks to deliver a reflective sensing system enabling application to a wider array of samples. With respect to the human body, there are many locations on the skin that are convenient to access for spot or continuous sensing, and there are locations that permit sensing discretely such that a worn sensor will not be visible. Other test subjects with a surface suitable for reflective interrogation include cuvettes, microfluidic trays, batch reactor windows, sampling chambers from continuous process reactors, and any type of liquid storage tank.

Reflective sensing greatly increases possibilities far beyond transmissive sensing on the human body. Unfortunately, with the benefits of greatly expanded choice of test sites comes the disadvantage presented as loss of constant volume interrogation. Establishing a constant volume interrogation with transmissive sensing is accomplished through compression to a fixed sample height onto the sample or skin. Over this controlled volume, we essentially count target analyte molecules for which we then determine an accurate analyte concentration.

Tissue is a complex turbid medium composed of different cell types and protein-rich extracellular matrix, which strongly impact the propagation of light. Absorption is the transformation of light energy to some other form of energy, such as heat, sound or fluorescence, as light traverses tissue and is quantified by the absorption coefficient, μa (cm−1). Absorption is the primary optical interaction that is exploited to measure analytes in human skin. In this turbid media environment, scattering is a major contributor to light attenuation and can confound attempts to measure specific analyte concentrations because skin is a highly scattering liquid with strong anisotropy. Scattering refers to a change in the direction of light propagation and is quantified by the scattering coefficient, μs (cm−1).

Figure 1:
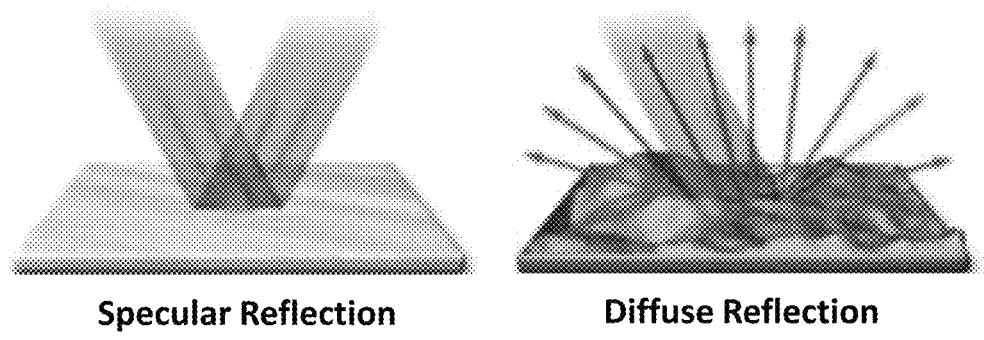
FIG. 1 illustrates the difference between specular and diffuse reflection.

Reflective sensing relies on emissive energy penetrating a sample, interacting with the sample constituents, and ultimately escaping from the sample surface, re-emission, for collection and detection. Optical energy imposed on the sample that experiences specular and diffuse reflection as illustrated in FIG. 1 provides no information in terms of absorption spectroscopy that would be useful for particular analyte assessment. So, with the goal of extending our prior transmissive noise cancellation methodology for analytes sensing in liquids to reflective sensing, efforts must be taken to ensure that the emitted, interrogating light energy has sufficient opportunities to travel through the sample, interact with target analytes, and then exit from the sample surface for detection. Compared to transmissive sensing, reflective sensing faces greater loss of signal intensity and quality leading to generally less precision for analyte concentration assessment.

Another consideration in applying our prior noise cancellation methodology arises with our chosen reference wavelength. Whereas with transmissive sensing, our reference signal, chosen for minimal absorption by the sample, performs quite well in passing through sample constituents or "skin elements", we face different optical phenomena. With our alternate and sequential pulsing applied to reflective sensing, the cancellation of scattering noise methodology does not change from our transmissive sensing art. However, a portion of the reference signal, by way of minimal absorption especially by water, continues to penetrate deeper into the skin, so to yield a comparative amount of light energy returned to the detector, power levels may need to be adjusted for optimum noise cancelling precision.

Therefore, with reflective sensing, our prior algorithms function slightly different from our transmissive sensing algorithms. Implementing reflective sensing requires that we adjust our laser driving parameters to coax as much reference and target wavelength energy back out of the skin as feasible within safety limits.

Figure 2A:
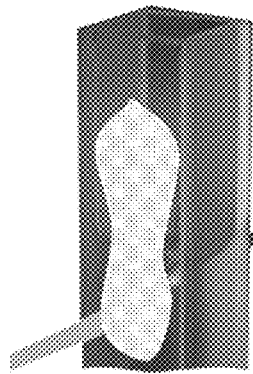
FIGS. 2A-C illustrate examples of an anti-reflective coating and a refractive index matching film and a liquid applied to rigid and non-rigid surfaces.
Figure 2B:
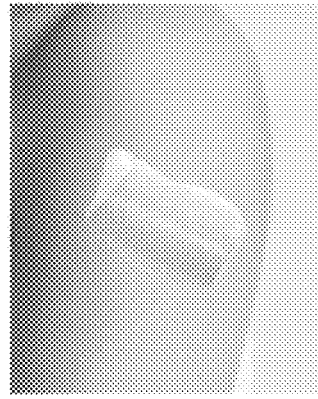
Figure 2C:

Several important configurations will enhance the data gathering results. Should the entry emission be on an angle, the detector(s) should be positioned to minimize receiving the bulk of pure specular and diffuse reflection energy as this carries no absorption information about the sample.

Where possible, the utilization of a refractive index matching material, i.e., film or fluid, should be considered to enhance the optical energy both entering and exiting the sample or skin. If using a container or cuvette to hold a sample, then an anti-reflective coating on the container should be considered to ensure that most emitted energy is not simply reflected from a smooth and possibly specular surface presented by glass, quartz, Plexiglas, etc. Examples of an anti-reflective coating and a refractive index matching film and a liquid are shown in FIGS. 2A-C. Some level of pressure applied to both the emitter and the detector optics during the sensing operation will enhance "air gap free" monitoring for consistent sensing performance.

With our absorption spectroscopy methodology, the goal is for the interrogating emissive energy to penetrate into the sample or skin and then return as much information, i.e., re-emitted optical energy, as possible to the detector(s). Adhering to as many of these conditions as possible will enhance for accuracy, reliability, and repeatability in measuring the target analyte wavelength energy absorbed by the target analyte molecules revealing the concentration of the target analyte in a sample container or skin.

Incorporation of Temperature Sensing

U.S. Ser. No. 18/114,414 describes a methodology for optimizing optical signal capture through dynamic matching of laser emitter center wavelengths to conditions matching the physio-optical sample characteristics by monitoring the sample temperature. Although not absolutely required, monitoring of the temperature of the sample under interrogation is good practice for precision optical sensing. The importance level of temperature monitoring is raised with reflective sensing because there is loss of sensitivity when switching from transmissive sensing to reflective sensing. The general rule is that the total potential captured signals from any sample by reflective sensing embody only 10 percent of that which might be captured with transmissive sensing. Therefore, temperature monitoring during the time of optical reflective sensing enhances overall accuracy by both optimizing interrogating light energy center wavelengths and functioning to support adjustment to the calibration curve, necessarily maintained, for each sample type or person whose analytes are being non-invasively measured.

Options for temperature sensing come down to optical scanning or physical contact of the sample with a thermocouple or digital temperature sensor. Optical infrared temperature scanning of the forehead is a medical industry standard. One surface scanning method has been proposed by Rockley Photonics' "Photonics-Based Measurement of Core Body Temperature," December 2021, however this method requires a level of optics integration, not only adding complexity, but drawing power that is dear in miniature portable equipment.

Thermocouples measure temperatures over a wide range, have quick response time, are rugged, durable, simple and have wide availability. A better choice, still, is an integrated digital temperature sensor using a diode or a transistor element for resistance or voltage output. Integrated means inclusion of signal conditioning circuitry that amplifies and processes the raw temperature data then converted into a digital signal by an internal analog-to-digital converter. Other benefits are factory-calibrated coefficients to compensate for any deviations and inaccuracies in the sensor's output, built in communication interfaces, memory storage, and 1 µA to 10 µA power draw while idle and a mere 100 µA while operating.

For sample or skin sensing, the contact surface of the digital temperature sensor needs to be brought in close proximity, ideally touching the surface being optically scanned. Any enhancement of contact such as with a thermally conductive interface—like a compliant, thermally conductive polymer or specially filled liquid—will improve temperature sensing accuracy.

Refractive Index Matching to Improve Light Transmission in and Out of the Sample Surface Use of refractive index matching materials will minimize the mismatch of refractive indices between emitter lenses that contact the sample or skin surface and the sample surface or skin itself. The material may take the form of a flexible or rigid film or a liquid. One of the earliest inventors to consider use of an index-matching medium is described in U.S. Pat. No. 6,152,876A where disposing a quantity of said medium between human tissue and input/output elements couples said elements to said analyte-containing tissue through said index-matching medium. U.S. Pat. Nos. 8,831, 700 B2 and 11,207,007 B2, the disclosures of which are specifically incorporated herein by reference, both proscribe placing or rubbing an index matching medium, such as glycerine, onto an area of skin under interrogation to "optimize the amount of light that enters and exits the skin."

Application of a film or liquid will always be considered an inconvenience and may not be necessary in many cases where sensor system accuracy is considered adequate or a trending function is considered as desirable when trading off cost and convenience issues. Nonetheless, any opportunity to improve consistency in delivery of as much emitter signal into the sample or skin is desirable for establishing conditions for utmost sensor accuracy.

Index matching films or liquids will bring benefits for both transmissive as well as reflective sensing. As we are working with two or more wavelengths with both the CVI and RODI methods, considerations must be taken such that the chosen refractive index value of the film or liquid works well with each wavelength.

Should an index matching film/fluid not be deployed with human skin, it is best to position the detector axis perpendicular to the sample surface to minimize capture of specular and diffuse reflection that carry little absorption data. Should a refractive index matching system be utilized enabling more of the emitter energy to pass into the sample or skin, then a more ideal position for the detector axis will be opposite the emitter and on a somewhat similar angle as the emitter beam is to the surface normal. These two configurations of emitter and detector angle are illustrated in FIGS. 3A and 3B.

Figure 4:
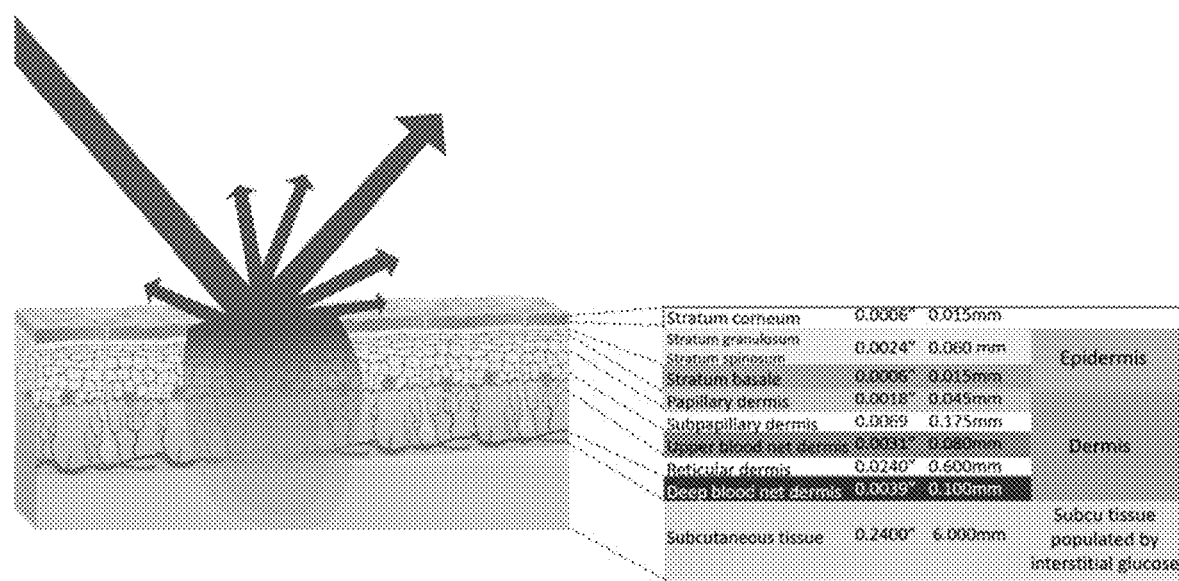
FIG. 4 illustrates the nature of light energy interacting with skin and details the composition of skin with dimensions portraying optical interrogation down to subcutaneous tissue.

Optically interrogating human skin for glucose concentration, as one analyte example, with reflective sensing presents multiple challenges. Here we see delineated in FIG. 4 the individual layers of skin and their dimensions. The subcutaneous tissue layer below the epidermis and dermis is predominantly where glucose molecules in interstitial fluid reside as they are moving from the capillaries and blood vessels into the interstitial fluid. Glucose molecules then transport into cells supporting their energy production needs.

Being able to interrogate down to this important subcutaneous layer is critical for precision measurement of interstitial glucose. Glucose molecules do reside in layers of the dermis and even the epidermis, but the concentration levels are less representative of the levels in blood and subcutaneous interstitial fluid.

For these reasons, clamping onto skin at the hand web and ear lobe for transmissive sensing helps ensure that the subcutaneous tissue with its complement of interstitial cellular and intercellular glucose are fully interrogated. By enhancing adequate depth penetration into skin, we ensure that reflective sensing can be as precise as possible for analyte concentration measurement.

To provide a basis of comparison, here is a brief overview of our transmissive sensing method for achieving accuracy and consistency. This proven basis for constant volume interrogation by transmissive sensing acts as a stepping stone to an optimize reflective sensing method in liquids.

Constant Volume Interrogation (CVI) involves compressing a flexible or liquid sample to a Fixed Height (FH) between the optical emitter and optical detector. This FH establishes an important parameter to the volume equation. The other parameters of the volume equation are the emitter beam diameter and the size of the typically round gathering lens in front of the detector element. The light scattering interaction in a transparent or turbid media is roughly an expanding cone. To establish a geometric volume for this CVI, the known factors are the emitter beam diameter, the FH, and the detector lens collector diameter. These factors define the volume equation for a truncated cone within which our transmissive absorption spectroscopy measurements are captured.

It is over this CVI that we count the number of analyte molecules of interest (AMI) through application of our Direct Infrared Laser Absorptive Scattering Technique (DI-LAST) as identified in U.S. Pat. No. 9,606,053 B1 which calls for utilizing a reference optical beam pulse followed by a target analyte optical beam pulse traveling the exact same path in the sample under interrogation, we use the ratio of the two values to establish an AMI concentration. Then by averaging a large number of AMI concentration values, the highest possible accuracy assessment of the AMI concentration is established. Quoting the Abstract of this earlier work:

A concentration of a chosen molecule in a liquid phase in a sample space is determined through use of a signal channel output/reference channel ratio obtained by use of an NDIR absorption technique in which scattering noise attributable to the liquid phase is reduced by alternately and successively pulsing infrared radiation from signal and reference sources which are multiplexed and collimated into a pulsed beam directed through the sample space containing the liquid phase and the pulse frequency is sufficiently fast so that a given molecule of the chosen molecule will not pass in and out of the sample space within the pulse frequency.

Transitioning from transmissive to reflective sensing dictates that we must now characterize the analyte molecular count over pathlength as a substitute for constant volume interrogation. We identify this methodology as Reflective Optical Depth Interrogation (RODI).

Reflective Optical Depth Interrogation (RODI) utilizes reflective sensing as compared to the transmissive sensing method of CVI where a volumetric interrogation condition can be established. This novel method of RODI creates a series of measurements that when plotted with a slope spectroscopy technique reveals a target analyte concentration level by association to an exact or similar sample type previously documented for a set of known concentrations. In this manner, we are now essentially able to count analyte molecules of interest (AMI) in a quasi-volume defined by the set of focal lengths establishing a set of interrogation depths.

Through the implementation of various lens systems that will be described herein, measurement of the reflected light energy from each depth is captured, analyzed and plotted for our Reflective Slope Spectroscopy sensing method.

Reflective Slope Spectroscopy is the only precision concentration measurement option for many types of samples where either one or all of these conditions exist:
1) solid, flexible sample, or liquid sample is too thick for adequate illumination energy to penetrate for a transmissive measurement;
2) there are underlying elements of the sample that prevent light transmission; or
3) particular sensor placement dictates the use of reflective sensing.

RODI also is dependent on the same alternate and sequential or simultaneous pulsing of a reference wavelength beam and a target analyte beam to accomplish the scattering noise reduction technique described in U.S. Pat. No. 9,606,053 B1.

In this disclosure, we are focusing on reflective only sensing employing our Direct Infrared Laser Absorption Spectroscopic Technique (DILAST) upon a single liquid surface enabling accurate, reliable, and repeatable reflective measurement for AMI determination.

Figure 5:
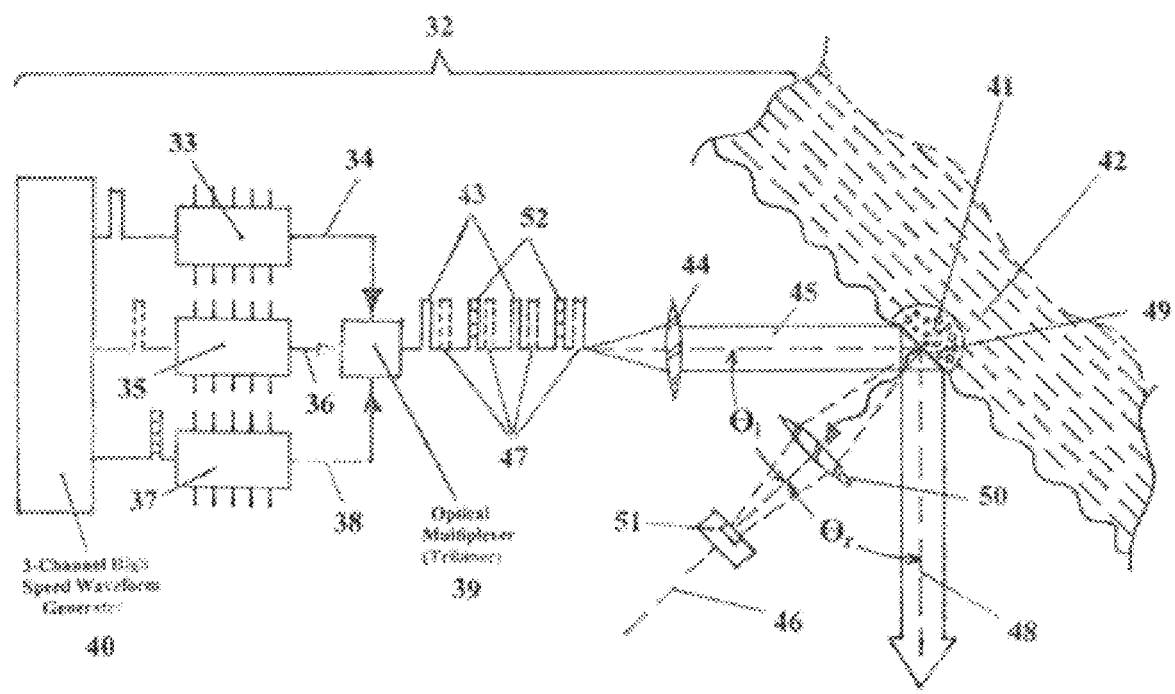
FIG. 5 is a reproduction of FIG. 10 of U.S. Pat. No. 9,823,185.

In one embodiment, positioning of the emitter beam should be at roughly 45° to the surface normal, and the detector axis can be on the surface normal above the illumination spot on the surface. If specular and diffuse reflection are reduced by the use of refractive matching materials, the detector axis may be positioned directly opposite to the emitter out to a maximum of 45° to the surface normal. One configuration is highlighted in FIG. 10 of U.S. Pat. No. 9,823,185 B1 which is reproduced in this disclosure as FIG. 5.

Figure 6A:
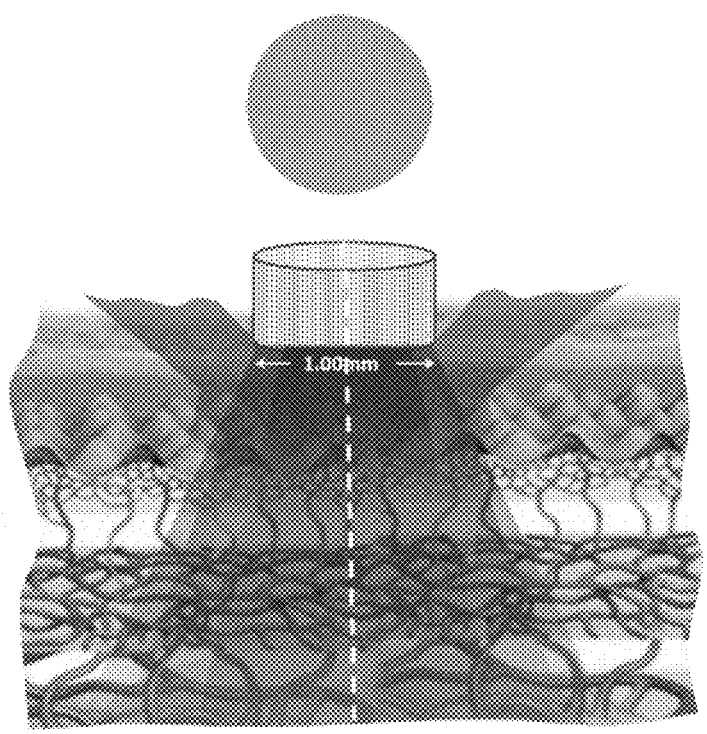
FIGS. 6A and 6B illustrate reflection of light from a surface when the light is entering perpendicular to the surface (FIG. 6A) and on an oblique angle of incidence (FIG. 6B).
Figure 6B:
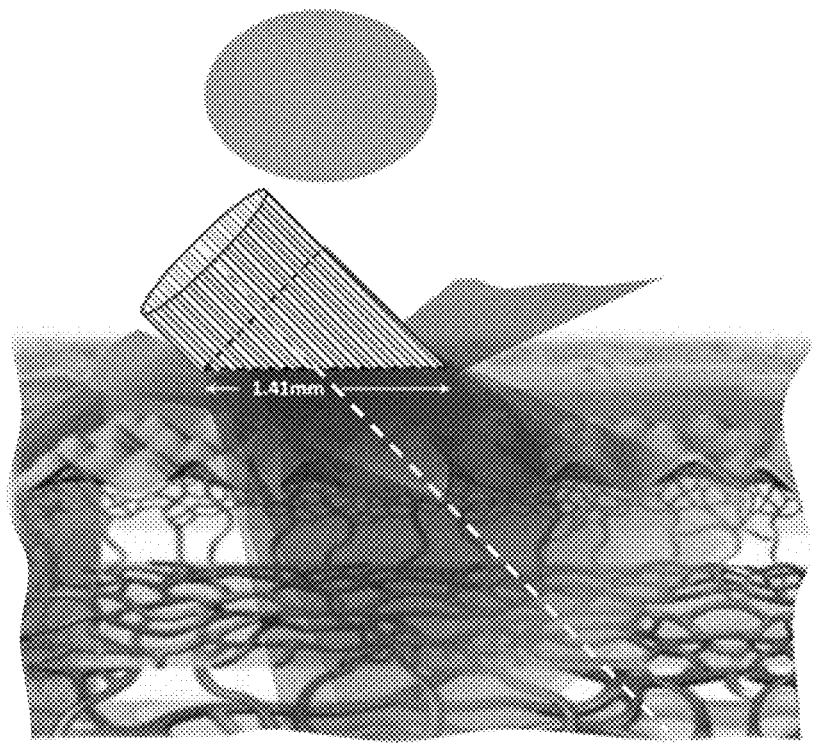

It is important to note that with an imposed light beam on an oblique angle of incidence, there is more reflection as the light encounters more variations with the larger surface illumination pattern leading to greater reflection and less total light entering into the skin. Examination of FIG. 6A with a perpendicular illumination pattern on the sample indicates the typical light reflection, scattering, absorption, extinction, and re-emission of light energy. Any other positioning than perpendicular of the imposing light beam, as illustrated in FIG. 6B, increases light reflection yielding less interrogation of the sample. Design and position of the detector lenses and detector element must take into account maximizing how the re-emitted light energy is captured for processing.

One implementation of RODI is accomplished through Reflective Slope Spectroscopy. The technique of Slope Spectroscopy is described in U.S. Pat. Nos. 9,939,373B2 and 10,876,961B2, the disclosures of which are specifically incorporated herein by reference. The methodology of these patents employs a fiber optic probe, as the sole emitter, being raised or lowered through a successive number of positions within a sample fluid chamber. The emissions from the probe are received at a detector located at the base of the fluid chamber. Measurements are plotted for each z-axis height of the probe with respect to the detector. The slope of this plot is then compared to the slope of a known sample set to determine the particular target analyte concentration. This seems to work in relatively simple liquids with a limited number of interfering elements. However, when addressing more complex samples such as mammalian skin, the complexity of interfering elements is quite large. For this reason, we use the dual beam system for scattering noise as well as additional light emitters that enable the tracking of interfering compounds that may change over time necessitating modification to the calibration curve of the sample for long term accuracy, reliability, and repeatability. The method employed for interference analyte tracking is presented in U.S. Pat. No. 9,726,601 B1.

The transmission sensing of analytes with Slope Spectroscopy establishes a controlled interrogation zone for each measurement on the plotted slope. This controlled optical interrogation zone is defined by the light energy emitter dimension, a known height between the emitter and detector, and a known size of the detector optics providing a specific volume for each measurement.

With our Reflective Slope Spectroscopy method, we do not enjoy the benefit of light passing directly from the light source to the detector. Our emitted light energy interacts with the liquid matrix in patterns of reflection, absorption, transmission, and extinction. Our received, detected, light energy is only that which re-emits from the sample or skin surface. We gather and focus, typically by reflectors and a collecting lens system, this light energy onto the detector surface. Monitoring of an analyte such as glucose resident in the cells, interstitial fluid, and blood in mammalian skin, in a reflective mode with precision, is a difficult challenge. Precision to the parts per million or better level is necessary for interpreting the small changes typically encountered when measuring a dilute analyte like glucose.

To achieve this precision, our novel Reflective Slope Spectroscopy technique establishes a quasi-volume for each measurement. With a single emitter and detector, we implement the use of multiple focal depths of light energy directed along the exact same optical path in the liquid sample or skin.

The invention can employ multiple lenses, each with a specific focal length, positioned precisely such that pulsed reference and signal beams follow the exact same axis through the liquid sample or skin. Detected values are converted to a concentration value through our ratio process that cancels out common Raleigh, Mie, and geometric scattering noise. The output value for each focal depth is plotted and compared to known values for various analyte concentrations in similar liquid matrix examples.

Controlling the Focal Depth of the Emitted Energy into the Sample

After describing the challenges with reliable and repeatable reflective sensing of a single surface of a sample and the methodology of Reflective Slope Spectroscopy, we move to methodologies for consistently establishing multiple focal depths within the sample for optical interrogation.

Perhaps the simplest method to address modifying the optical focal distance to which the emitted energy of our system is directed into the sample or skin is a variable focus lens system.

Figure 7:
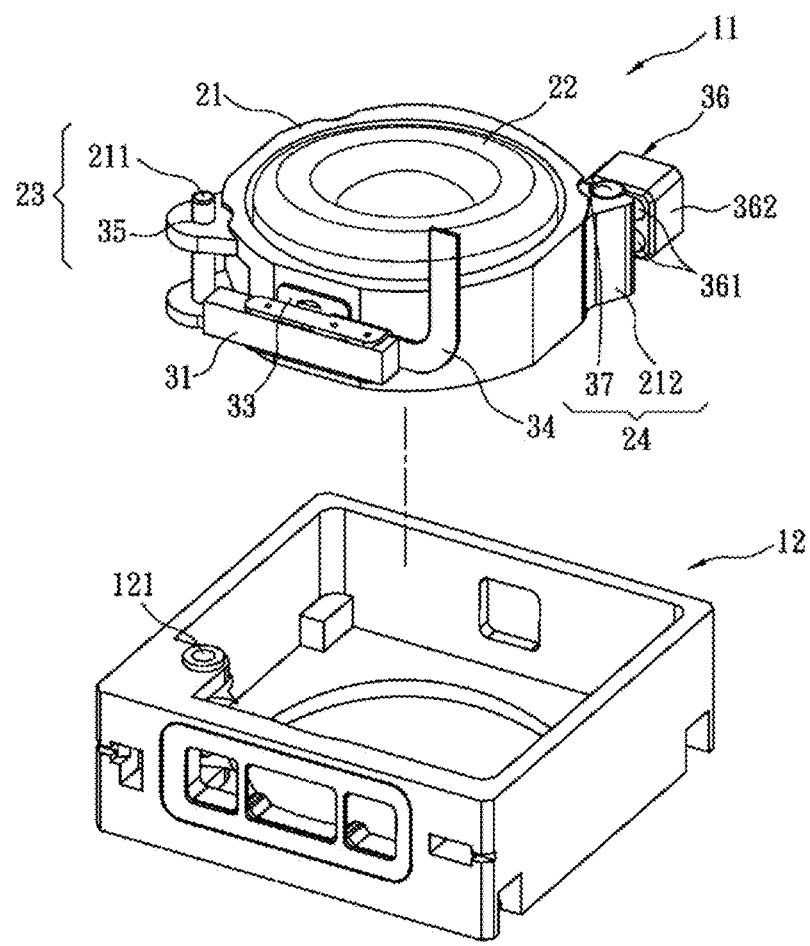
FIG. 7 represents FIG. 6 (Prior Art) revealed in U.S. Pat. No. 7,936,527 B2 for a compact auto focus lens module based on a piezo actuator.

There exists considerable art in how the variable focus function can be accomplished. Most suitable to a compact handheld or patch module is a newer compact auto focus lens module shown in FIG. 7. The main elements of this piezo actuator revealed in U.S. Pat. No. 7,936,527 B2 (illustrated as FIG. 6 (Prior Art)) include a lens barrel 21, an optical lens set 22, piezoelectric actuator 31, a tangent thrust element 36, a metal member 33, a guiding fixture 23, and a sliding fixture 24. The lens barrel driven by the movement of the piezoelectric actuator moves along the optical axis under controlled guidance with fewer elements, compact volume, and light weight achieving fast movement, stable focusing and reduced tilting. Other examples of this art for compact focusing are found in US2008/0013196, U.S. Pat. Nos. 6,594,450, and 7,145,738.

Figure 8:
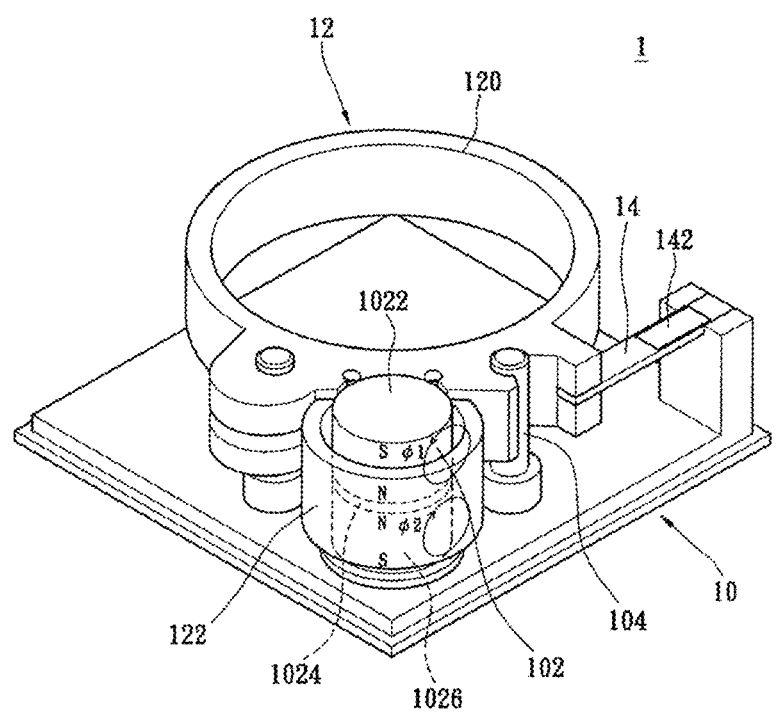
FIG. 8 presents FIG. 1 (Prior Art) as the leading diagram in US2008/0246353 etc., where a focusing optical lens set is driven by a Voice Coil Motor (VCM).

One movement method for a focusing optical lens set is by Voice Coil Motor (VCM) as demonstrated in US2008/0013196, U.S. Pat. Nos. 6,594,450, and 7,145,738. FIG. 8 presents FIG. 1 (Prior Art) as the leading diagram in US2008/0246353, etc., where a focusing optical lens element 120 is positioned by electrified action of voice coil element 102.

Figure 9:
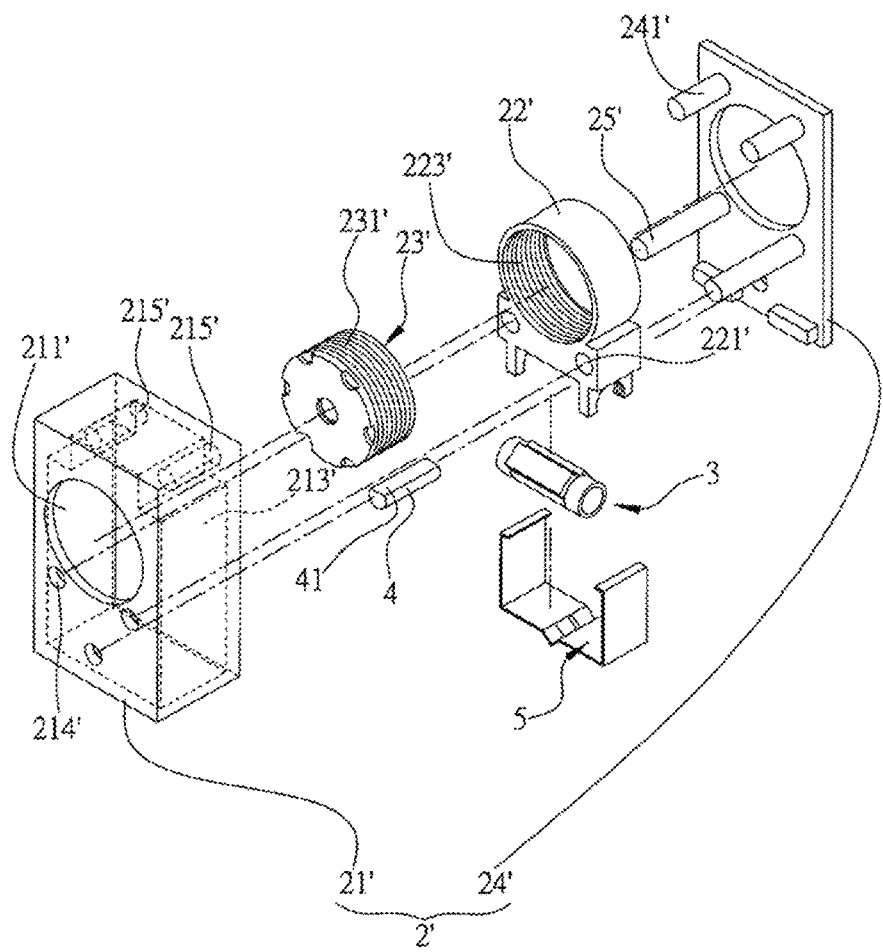
FIG. 9 shows FIG. 8 (Prior Art) revealed in U.S. Pat. No. 7,480,109 B1, US2008/00851, etc., as a piezoelectrically driven optical lens module.

FIG. 9 shows FIG. 8 (Prior Art) revealed in U.S. Pat. No. 7,480,109 B1 and shown in US2008/0174889 as a piezoelectrically driven optical lens module. This module includes a guiding rod 4 having a frictional surface 41, and a piezoelectric actuator 3, mounted in an elastic element 5 so as to drive the lens set 231' as well as the lens barrel 22' to move along a guide pin 25' by a guide slot 221' for focusing.

Figure 10:
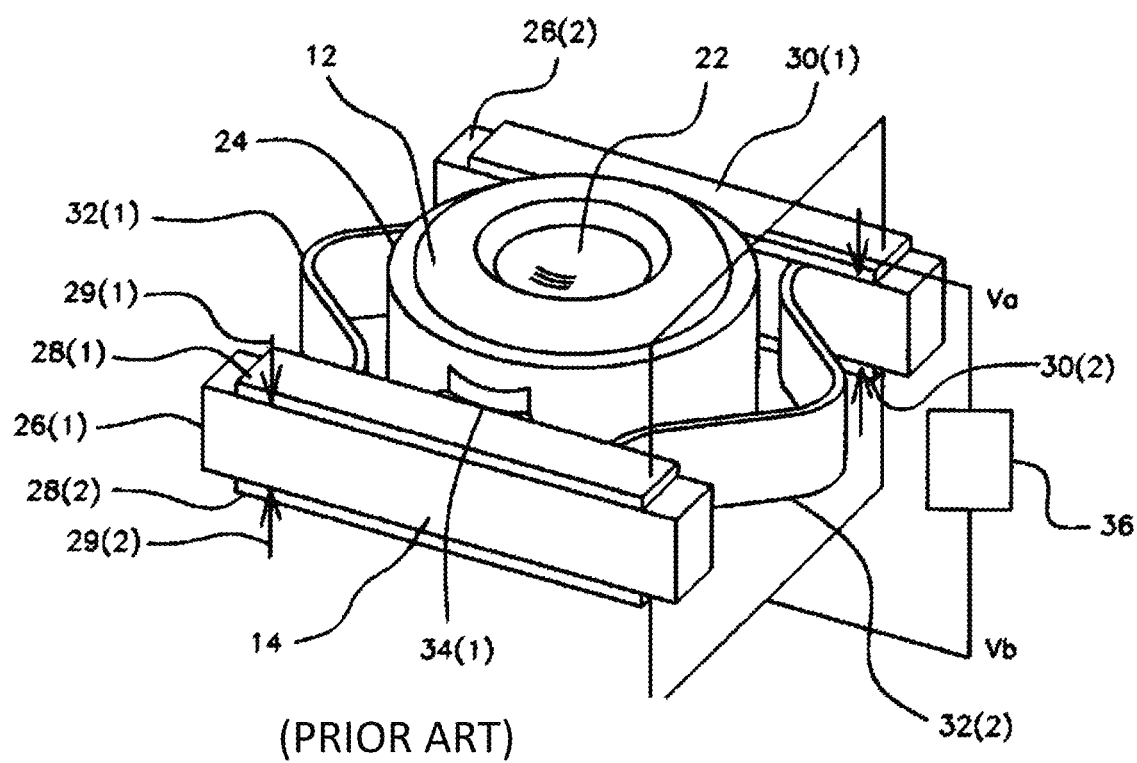
FIG. 10 incorporates FIG. 2A (Prior Art) within US2008/0231970 A1 where an UltraSonic Motor (USM) creates a movable system.

Ultrasonic motor (USM) is another type of electric motor formed from the ultrasonic vibration of piezoelectric material that is deformed upon application of a voltage as prior arts disclosed in US2009/0153987, US2008/0297923, US2008/0174889 etc. FIG. 10 makes reference to FIG. 2A (Prior Art) in which, as revealed in 2008/0231970 A1, the ultrasonic motor is applied to auto focus a lens module. This assembly consists of a plate spring 32 which applies an elastic force against two piezoelectric actuators 28, generating a friction force between a guide rail 34 and a lens barrel 22.

Figure 11:
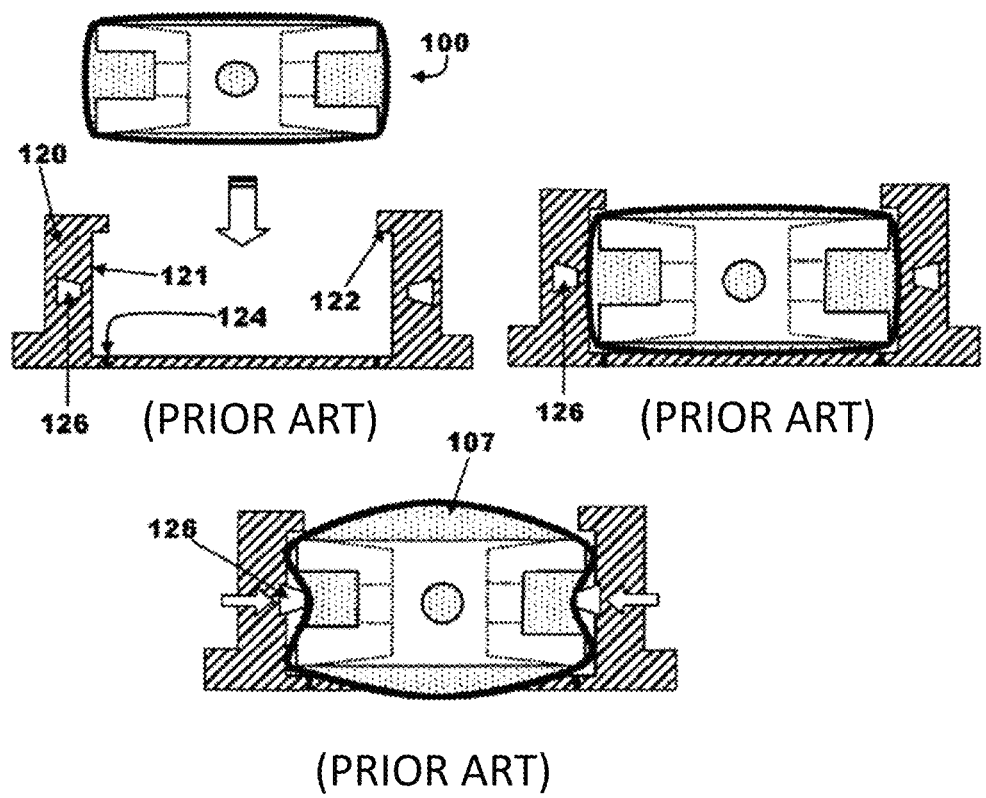
FIG. 11 shows FIG. 2A-C (Prior Art) as one configuration in U.S. Pat. No. 7,646,544 B2 of a lenslet acted upon by variable pressure from a circumferential sidewall force.

Other variable focus technologies involve use of liquid manipulation to shape lenses. FIG. 11 shows FIG. 2A-C (Prior Art) which is one configuration in U.S. Pat. No. 7,646,544 B2 presenting various optical lens designs all adjustable by fluidic manipulation. In this illustrated version, a lenslet is acted upon by variable pressure from a circumferential sidewall force.

An applied voltage in FIGS. 12A and 12B establishes deformation of one or more surfaces containing a liquid changing the optical focus where FIG. 12A represents a deeper focal length and FIG. 12B a shallower focal length. It is unlikely that such gross lens shape modifications would deliver the extreme precision that we envision needing for our controlled depth interrogation needs for now. The future, however, may enable suitable miniaturization and precision with this art.

All of these variable focus solutions are possible to serve our needs of delivering specific focal depths for light energy interrogation. An important benefit with variable focus is the ability to optimize the particular focal depths for each sample or skin under interrogation. Disadvantages with variable focus are the multiple components and tolerance stack-ups that may affect the ultimate reliability and repeatability of our sensor system.

An option to simplify the emitter optical depth focus control is to employ individual lens, lens assemblies, or a molded lens systems that incorporates two or more lens elements into a single body to deliver specific focal depths. There are a number of configurations with which we can deploy these individual lenses. Challenges lie in how these multiple lenses can be fixtured and moved such that we maintain DILAST requirements that the emitted light for both the reference beam and AMI beam remain on the same axis of penetration into the sample or skin. In this manner, we adhere to maintaining a relationship of common interrogation zones for each set of measurements.

Fixed Lenses and Lens Configurations

Fixed lens types that will work with our RODI system to provide a fixed optical depth include a range of design shapes as well a number of materials of construction. Fixed focal point lens types include refractive single and stacked lens assemblies and flat optics metalenses. Materials of construction include glass, plastic, quartz, etc. For the new generation of meta lenses, often manufactured with semiconductor processes on wafer like substrates, may include a further range of materials inclusive of and not limited to polysilicon, CMOS, germanium, gallium arsenide, and titanium dioxide.

Figure 14:
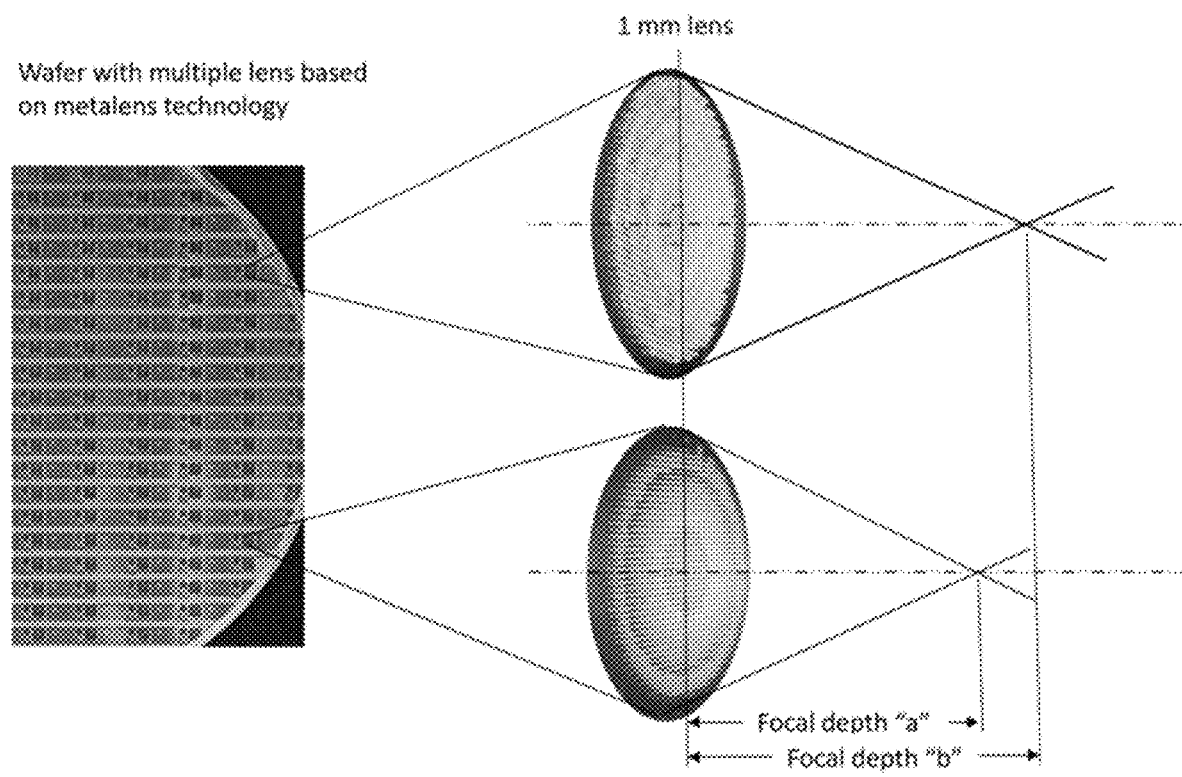
FIG. 14 illustrates two 1 mm diameter metalenses.

Of particular application to our system miniaturization goals are metalens designs. The precision mass production aspect of metalens as well as their flat aspect portend to meet optical performance, customization, and cost goals for RODI implementations. Metalens technology relies on material properties to create a converging wavefront. Shown in FIG. 14 are two 1 mm diameter metalenses. Each lens design uses numerous micro pillars of sometimes changing material composition working in concert to redirect light in a very precise manner.

Important considerations in the lens choice, beyond pure dimensions, is the suitability for post application of various coatings to the lens body to achieve levels of anti-reflection and modifying the index of refraction such that matching can be done to the nature of the sample or skin under interrogation.

Figure 15:
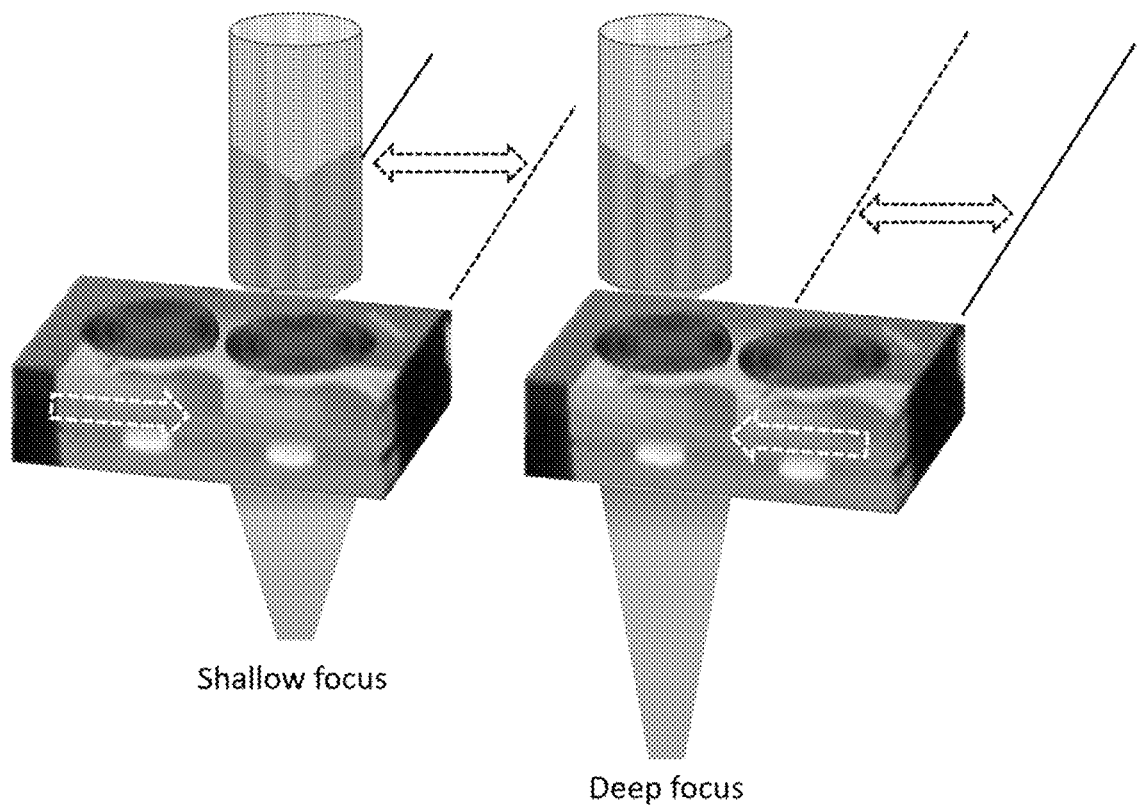
FIG. 15 illustrates the use of two lenses which are moved linearly by a lens carrier.

The most basic design for implementing RODI incorporates just two lenses configured as shown in FIG. 15 where a lens carrier is moved by voice coil motor, piezoelectric motor, or screw drive rotary motor. One lens delivers a shallow focus and the other lens delivers a deep focus into the sample or skin. This simple lateral motion to bring each lens in alignment with the emitter beam becomes more complex as additional lenses are added to the lens carrier.

Figure 16:
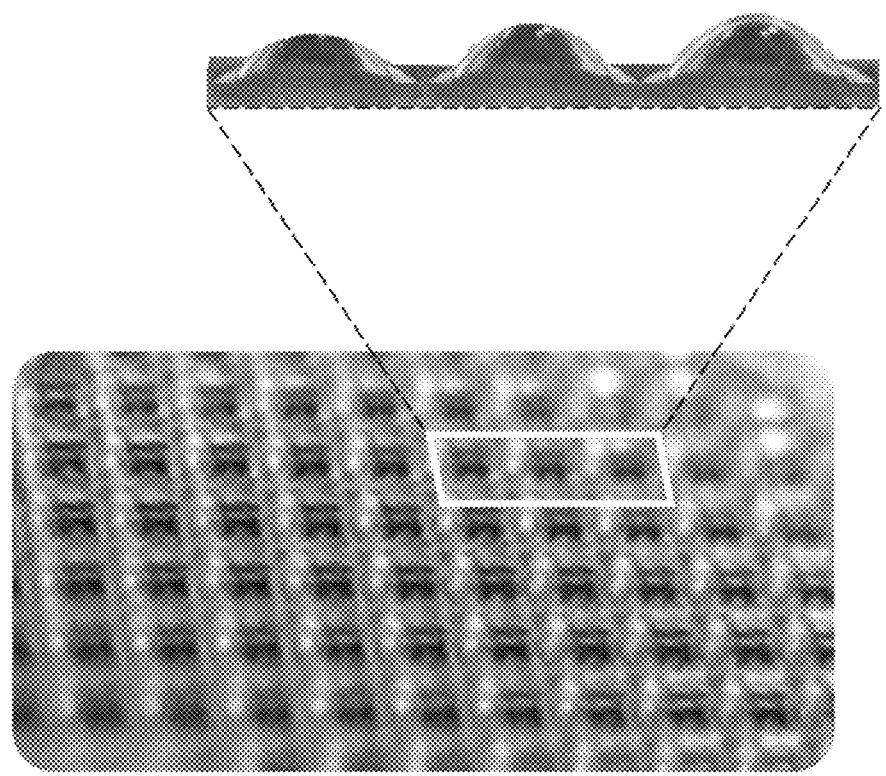
FIG. 16 illustrates the concept of a micro-molded lens set.

In FIG. 16, the concept of a micro-molded lens set is presented. The art of micro-molding has progressed substantially to meet the volume and precision needs of cellphone optics. Here, a three-lens set example is produced as part of a single molded array. Post molding, curing, and coating of various materials can be accomplished with minimal handling. Then the array is accurately diced into final shapes for use in the sensor optics.

Figure 17:
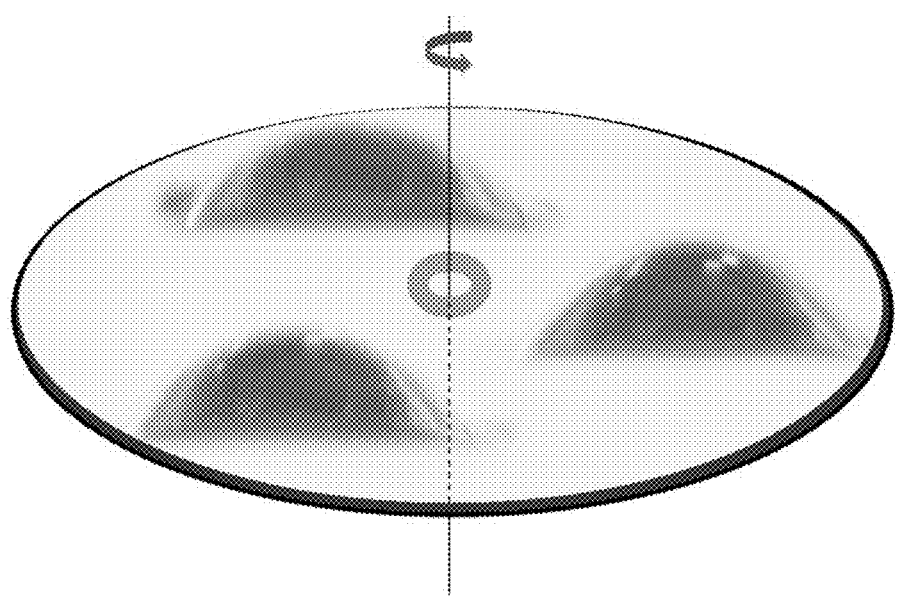
FIG. 17 illustrates a round grouping of lenses that might be rotated into alignment.
Figure 18:
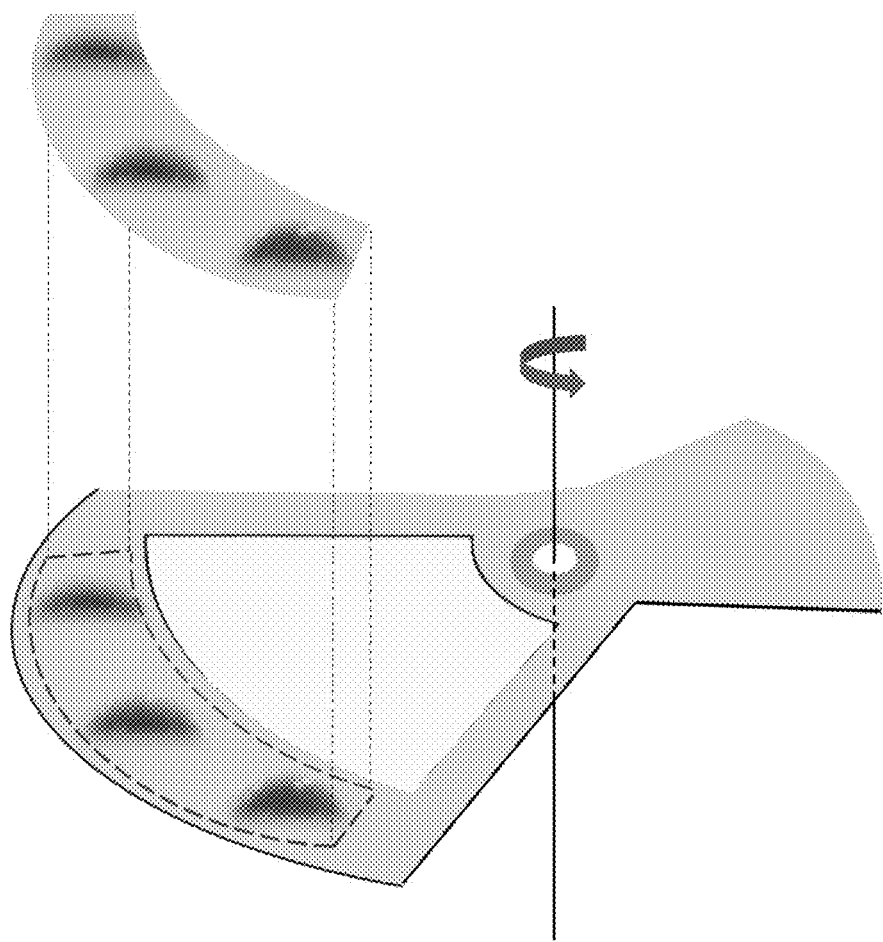
FIG. 18 illustrates a curved grouping of lenses that might be mounted onto a rotating turret.

Presented is a rectangular array, but the lens set could be in any configuration. FIG. 17 presents a round grouping that could be rotated around one central axis to move each lens into the common illumination path. FIG. 18 describes a curved grouping of lenses that would be mounted onto a rotating turret that moves the lens set in an arc to position each lens into the proper illumination path. A rotary turret offers the ability to include multiple lenses in a compact footprint. The lens turret design moves the axis of rotation away from the illumination emitter area for options with size reduction for portable sensor configurations.

Extreme miniaturization can be accomplished by locating the emitter and detector elements as close together as optically useful and physically possible.

Figure 19A:
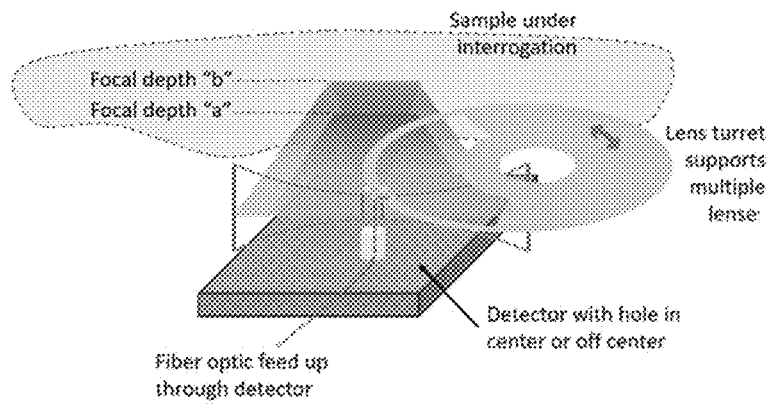
FIGS. 19A-D describe miniatured approaches to optical packaging with FIGS. 19A-C presenting and collecting light perpendicularly to the sample surface and FIG. 9D presenting an off-perpendicular approach.
Figure 19B:
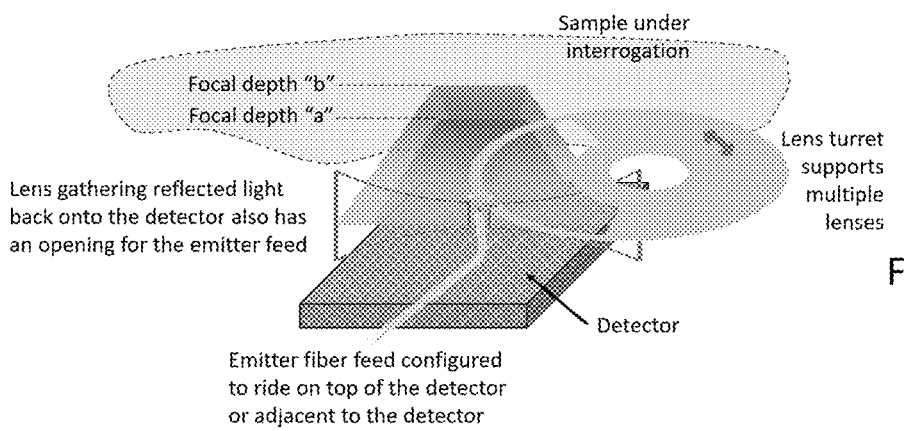
Figure 19C:
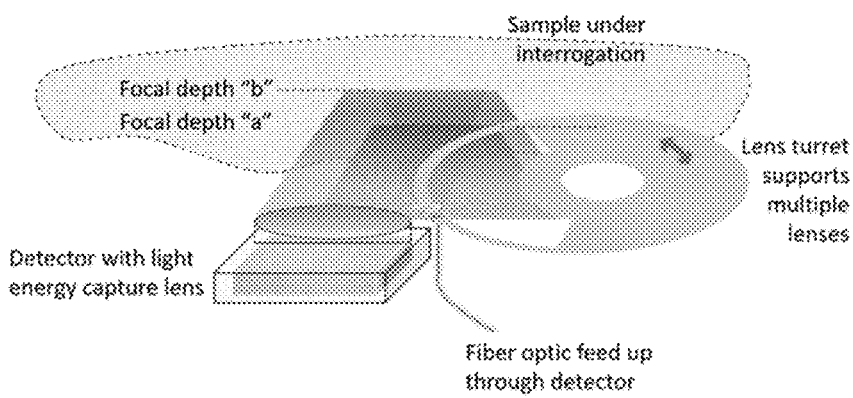
Figure 19D:
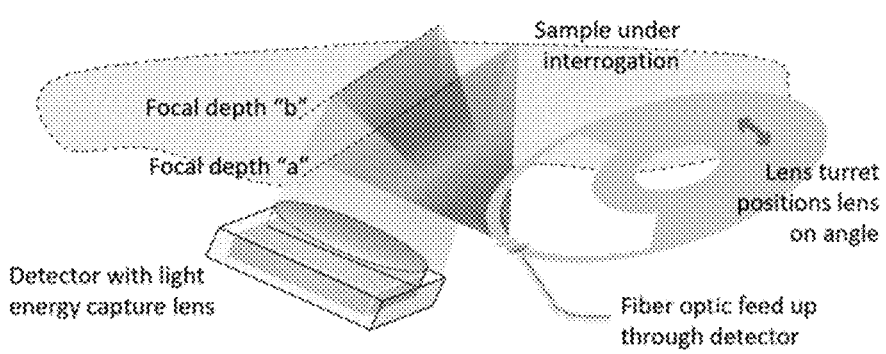
Figure 20A:
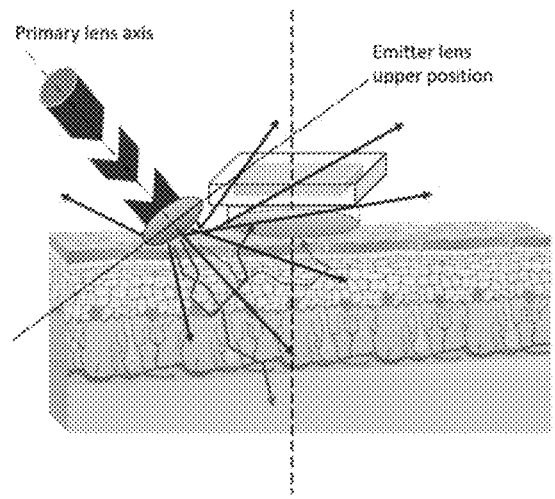
FIGS. 20A-D describe optical interrogation configurations where only a single focusing lens is utilized. By mechanically raising or lowering the lens, an effective change in focal depth interrogation into the liquid matrix is established.
Figure 20B:
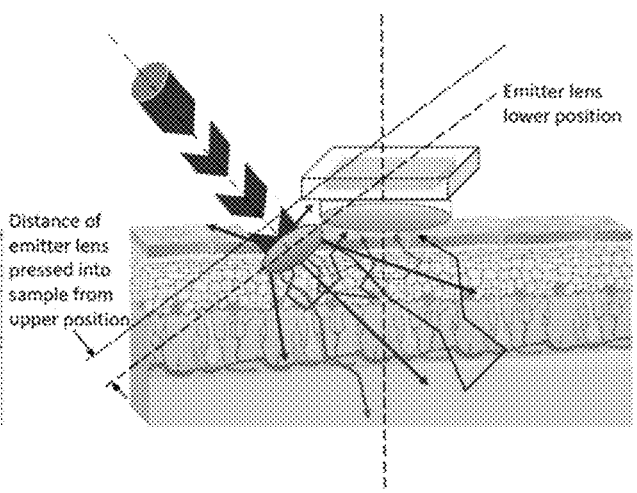
Figure 20C:
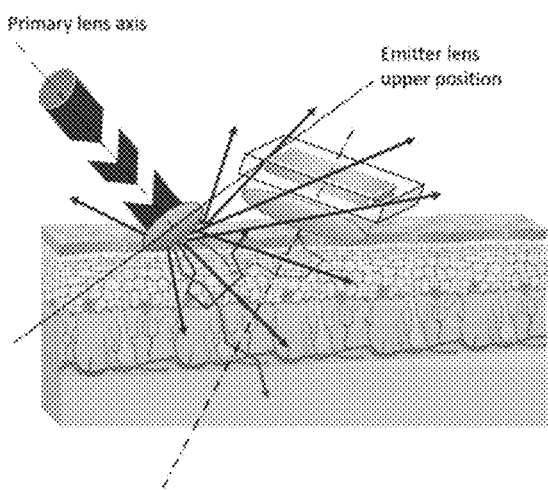
Figure 20D:
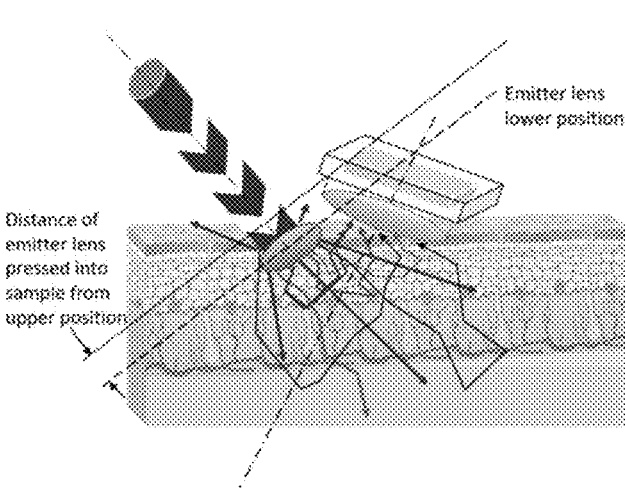

FIGS. 19A-D are miniatured approaches to the optical packaging challenge. FIGS. 19A-C present and collect light perpendicularly to the sample surface and FIG. 19D presents an off perpendicular approach.

FIG. 19A details a configuration where the emitter is a fiber optic feeding directly through the detector element. The rotary lens turret positions the focusing lens set over the fiber optic emitter with as little blockage as possible for the returning light collected by the detector system.

FIG. 19B simplifies the detector design by eliminating a via opening. Here the fiber optic feed is adjacent to the detector and configured to ride on top of the detector, which also reduces the overall size emitter/detector footprint.

FIG. 19C offsets the rotary lens set away from the detector maximizing the opportunity for full re-emitted light collection.

FIG. 19D presents an off-perpendicular axis approach to both the emitter beam and the detector light collection system. When placing the emitter beam on an angle, the number of effective focal depths will be increased by geometry before light energy is absorbed by optically denser components such as muscle and bone underlying skin. The emitter beam and the detector axis may reside at various angles to one another for performance optimization of the sensor system.

The set of FIGS. 20A-D describe another optical interrogation configuration where only a single focusing lens is utilized. By mechanically raising or lowering the lens, an effective change in focal depth into the liquid matrix is established. Only two positions are represented, but the mechanical motion could create a number of distinct focal depths for the reflective absorption spectroscopy data collection. The initial position may be above the liquid matrix surface with subsequent lower positions actually pressing into the liquid matrix. For FIGS. 20A and B the emitter axis is non-perpendicular to the liquid matrix and the detector system is positioned to receive re-emitted light energy in a perpendicular arrangement to the liquid matrix. A dotted line indicates the lowered lens position with respect to the surface of the skin.

For FIGS. 20 C and D, the emitter axis is non-perpendicular to the liquid matrix and the detector system is also position in a non-perpendicular arrangement to the liquid matrix. With the dotted line indicating the lowered lens position, it is apparent that having the detector system slightly further away from the raised and lowered single lens will allow less constricted movement of the skin as various focal depth interrogations are processed for analyte concentration scanning of the skin.

Each of these emitter/detector configurations establish their own photon scan volume controlled by particular conditions of the media being scanned. This presents many variables that affect measurement of concentration of a particular target analyte or AMI. An examination of optical sensing history reveals many attempts to make accurate reflective concentration measurements of analytes by way of many spectroscopic methods. These various spectroscopic methods include Ultraviolet (UV), Near Infrared (NIR), Mid-Infrared, Far Infrared, Raman, Evanescent Wave, Fluorescence, Impedance, Kromoscopy, Occlusion, Optical Coherence Tomography, Photoacoustic, Photothermal Deflectometry, Wave-mode Differential Laser Photothermal, and Binary Phase Masking.

Visualization cannot be discounted in understanding the difficulty of the optical sensing task for analytes in a complex liquid matrix. FIG. 21 portrays our environment for transmissive sensing with a controlled interrogation volume set by a consistent clamped height of typically 3 mm through which this is considerable light energy received at the detector element. Compare this now to FIGS. 22A and B portraying reflective sensing of the same sample. Chevrons indicate approximate multiple focal depths of the interrogating emitter light energy into the complex liquid sample. Ultimately, electro-optics balancing and optimizing input energy to the greatest re-emitted light energy reaching our detector element. FIG. 22A illustrates a perpendicular emitter minimizing specular reflection and FIG. 22B presents the emitter off a perpendicular axis that provides opportunity for more focal points in the complex matrix from which individual measurements can be captured for application into our Reflective Slope Spectroscopy system.

The functioning of an absorption spectroscopy system is limited by the physical realm of wavelengths vs absorptions of the sampled matrix. FIG. 23 helps to visualize how absorptions between different wavelengths relate to their penetration depths. Shown are three focal depths of 1.5 mm, 2.0 mm, and 2.5 mm imposed on the liquid matrix with our reference and target analyte wavelengths. With a target analyte wavelength of 1150 nm, we will reach an ultimate depth of penetration of 5 mm. However, with our reference wavelength of 1064 nm, the penetration depth is 10 mm and beyond. These physical aspects impact how much light at each wavelength returns to the liquid matrix surface for reflective sensing. Optimum optical return energy collection with both imposed optical light beams is a balancing operation of power levels, frequency, and duty cycles of each pulse pair.

In this disclosure, we present a new absorption spectroscopic sensing method based on detection of reflected energy from a light absorbing surface. This methodology establishes a quasi-volume through variable depth interrogation by way of optical lens manipulation. The AMI count numbers obtained for each interrogation depth are plotted and an intersecting slope established that is compared to a known calibration set for a given sample to deliver an accurate concentration assessment of the AMI in the sample.

Our methodology may utilize any of three configurations for controlling our optical interrogation depths with reflective sensing. Two involve lenses that supply different focal depths in the sample and the third relies on a mechanical means of modifying the scan depth all while adhering to the tenets of U.S. Pat. No. 9,606,053. This patent directs that the reference and target analyte (AMI) interrogation beams must travel the same path through the sample. This implies that when a single focusing lens is employed, it must incorporate an adjustable focus feature of some nature to maintain the single path alignment while scanning at multiple interrogation depths. The second configuration incorporates multiple lens, each with their own unique focal depth along with a physical means to move each lens such that when focusing the emitter beams are pulsed, the lens' primary axis is at one location for proper interrogation. A third configuration employs only a single lens assembly with a single focal depth. This lens assembly is mechanically moved vertically, along the primary lens axis, from one position to another such that it compresses into the sample in one or more steps. This stepping motion effectively changes the effective focal depth into the sample for establishing the quasi-volume measurement conditions.

Consistency is paramount to achieving sensing accuracy for each and every set of measurements. With each lens focal point, we capture a series of reference and AMI sequential absorption value pair ratios. Then, by adjustable focusing, lens change, or mechanical movement of a single focal point lens, a second set of reference and AMI sequential absorption pair ratios is gathered. This data gathering may be repeated as necessary based on the focusing capability, number of lenses, or physical distance that the lens can be compressed into the sample.

For each focal point in the sample, a Focal Point Set (FPS) is established. This FPS is the set of reference and AMI sequential absorption pair that are ratioed and averaged over a number of pair sets, typically ranging up to 10,000 pairs for increased sensing precision.

The FPS values for each "interrogation depth" are plotted onto a graph and the slope of the line running through these data points can be matched to a specific AMI concentration established through a prior calibration procedure. The results of that calibration procedure enable matching the slope of the FPS values to a known slope value related to a range of AMI in a known sample or previously tested individual. Of importance is that the particular interrogation wavelengths and RODI configurations are consistent to those used for the calibration procedure whether it be with a known sample or particular individual's skin representative from where future sensing measurements will be taken.

One example we can examine with RODI is measurement and long-term monitoring of glucose molecules in the interstitial fluid of human skin. The calibration process for establishing accuracy in measuring glucose can be accomplished using the same reflective sensing setup along with an individual's standard fasting process followed by a glucose tolerance test as described in U.S. Pat. No. 10,241,044. At the beginning of the fasting test optical measurements are compared (ideally) to blood draws sent to a Xylem (Yellow Springs Instrument) benchtop glucose monitor or other gold standard blood sugar measurement platform, as well as an approved finger stick strip & reader combination for use with blood drops placed onto a test strip resident in an electronic reader. Note that many blood sugar test strip vendors initially have met the FDA standards that require roughly +/−15% accuracy, but they have been seen to vary in the field. So, it is imperative to seek test strip and meter combinations from a vendor who has demonstrated accurate performance post FDA approval for the calibration process.

Airware's RODI method enables reflective sensing from a single surface. RODI relies on comparison of two or more measurements within the exact same scan zone axis differing only in the focal depth for which the measurements are taken. Here in FIG. 24, comparative absorption data from our reference and target analyte sequentially pulsed lasers is captured and averaged for each focal depth. Two or more focal depth absorbance values are plotted with Absorbance vs Focal Depth. The slope of the line running through these data points is then correlated to a calibration standard set for each sample or skin type. Unlocking path length as a variable, the slope of the resultant line from two or more sets of depth measurements is directly proportional to the AMI concentration in the sample or skin.

Important to note is that Airware's RODI methodology can be employed with a wide range of optical wavelengths, not limited to UV-based illumination as in U.S. Pat. No. 10,876,961. The essence of applying RODI is that the reference wavelength and AMI chosen wavelength have:
1) reasonable depth penetration of the sample or skin;
2) reference wavelength exhibits minimal absorption by the bulk of the constituents within the sample or skin; and
3) when the AMI absorption value is ratioed to the Reference absorption value for a particular
   a) alternate and sequential pulse pair with a single detector; and
   b) simultaneous pulse pair with more than one detector element that common Rayleigh, Mie, and geometric scattering noise is minimized enhancing the sensitivity of detection of the AMI.

Determination of an analyte concentration using RODI is based on the Beer-Lambert law and our derived Reflective Slope Spectroscopy equation: $m=\varepsilon c$ where m is the slope of the regression line by plotting the delta of target analyte peak detection to reference wavelength peak absorption as a function of optical path length, $\varepsilon$ is the extinction coefficient, and c is the sample concentration. This method relies on establishing a reference slope from a calibration procedure. The sample concentration can be calculated using the following equation:

$$c_{target\ analyte} = \frac{m_{target\ analyte} c_{calibration\ slope}}{m_{calibration\ slope}}$$

where $c_{calibration\ slope}$ and $c_{target\ analyte}$ are concentrations of the calibration sample and of the target analyte, respectively, and $m_{calibration\ slope}$ and $m_{target\ analyte}$ are slopes of the calibration experiment and the plotted slope of the delta values of the target analyte to reference absorption as a function of optical path length, respectively. The slope of this plot in FIG. 24 of Absorbance factor vs. Focal Depth is then matched to a known database of slopes for specific samples and skin types. A selection of developed databases is represented in FIGS. 25A, B, and C developed for a range of analyte concentration. For this example, in FIG. 24, the slope most closely matches FIG. 25 B from the developed database that represents a glucose value of 127 mg/dl.

This extensive database is generated by large test programs of measurements of dosing levels with representative samples. For human skin, there are suitable complex tissue phantoms that can be created to match a wide array of human skin conditions. These conditions include melanin content, body mass index representative of a fat content in skin, hydration level of skin, and age of skin that relates to both the thickness of skin and the surface condition from young smooth skin to older skin with levels of skin irregularity like wrinkles.

Once a slope is best matched to the known database, the target analyte concentration can then be reported. For human glucose levels, this would be reported as mg/dl or mmol/l.

Personal calibration databases can be established, as well, for enhancing precision as ongoing measurements can be checked against standard tests. With this building of personal databases and potential collective sharing of blinded data, slope databases can become increasingly granular and precise for accuracy, repeatability, and reliability of measurements of target analyte concentrations.

Now with the Reflective Slope Spectroscopy methodology, a review of various optical hardware considerations to deliver the precise pulsed, narrow-band light energy for reference and target analyte beams to the sensing surface, and considerations to include refractive index matching, there still remains considerations to best manage delivery of light energy into and back out of the sample or skin surface with modulation of power levels.

RODI Based on Modulated Emitter Power Levels

All of the configurations described for establishing variable focal lengths for guiding controlled radiation into a sample or skin will deliver possibly valuable concentration data by modifying the emitter power levels. Modifying emitter power levels may also enable the use of a single lens with a single focal distance for sample or skin reflective sensing. Always being conscious of preventing any damage caused by heating or other radiative effects, there is a range of power levels over which the alternate and sequential narrow band lasers can operate safely with reflective sensing.

For optimum system reliability and repeatability, we typically look for simplicity. However, constant modifications to the laser operating conditions do present electronic controls issues as well as challenges in quality control testing for this wider range of operating conditions. Fortunately, all of this may be overcome with added benefits of adjusting the entire pulse power regime to match that of the specific sample or skin under interrogation.

With a single lens/single focal depth design, increasing the pulse power of the target analyte laser from 4 mW to 8 mW increases the number of photons entering the interrogation space. FIGS. 26A and B illustrate how the illumination depth and width will grow with more photons flooding the interrogation space. Differences between detected values from the 4 mW pulses and from the 8 mW pulses can be mapped to a modified slope concentration plot where the horizontal axis is now emitter power level. And in turn, the slope is correlated to the AMI concentration.

Of note with our DILAST method, increasing power levels will not always deliver better data. To best manage scattering effects in liquids, a goal is minimizing the total noise of the system. When we ratio our reference to target analyte absorption values detected specifically to minimize scattering noise to obtain the purest sensory information on the target analyte concentration, increasing the emitted energy into the sample or skin is essentially adding more noise. Hence, adding more total photons will not necessarily increase the precision of the sensor measurement. It is a matter of best managing the balance of the photons between the reference and AMI emitters for optimized noise cancellation.

Important whether using power levels or optical manipulation for reflective sensing is maintaining very consistent emitter power levels. These levels will need to be controlled over the typical power capabilities of NIR lasers operating from sub-mW up to 200 mW levels. Control of the power levels is through a system of photodetectors tightly optically connected to the set of emitting lasers.

As our DILAST art continues to advance, expectations are that variations of power levels of the applied reference and target analyte lasers will be a powerful factor in extending the technology to a wide range of analytes in liquids.

In addition, variations in power levels may become a part of the initial calibration function where the optimum operating regime for the emitting lasers can be best matched to every individual's skin type to overcome many factors such as melanin content, hydration level, body mass index, and skin age providing the absolute highest accuracy in sensing AMIs.

The present disclosure has focused on a new technique for reflective sensing. To help better advance this art, we will now address some potential sources of error in the technique already described.

Extending the volume of the interrogation zone with RODI may increase the opportunity for motion artifacts to have a greater impact on sensing accuracy. To counteract motion artifacts, accomplishing the multiple depth data gathering functions as quickly as possible will optimize overall system accuracy. Limitations here are the recovery times of the detector element and the speed with which adjustable focal depths can be accommodated. The optical pulsing control and detector capabilities are probably an order or two of magnitude faster than any mechanical system. So, optimization for motion artifact reduction should center on speedy methods for focal depth shifting.

Other errors relate to tolerances on the physical movement of the lenses. With the use of a single lens pressed into the sample or skin at progressive distances, repeatable depth control may be a challenge based on the stiffness and possibly temperature of the sample or skin. In other versions of RODI based upon the use of the alternate lens changing mechanisms, tolerances will arise for aligning each lens primary axis to the emitter beam central axis.

And with respect to variable focus lens systems, certain motion creation devices like stepper motors and piezoelectric motors can deliver extreme precision, but liquid lens focusing systems may lack the necessary precision.

The actual lens production brings its own set of tolerances that will require robust inspection systems before elements or lens sets are installed into the sensor system which must then go through extensive functional test for system level precision.

Consideration of Melanin Content of Human Skin

Another known interference factor for absorption spectroscopy in human skin is the presence of melanin. Melanin is a relatively broadband absorber from 400 nm through to 1400 nm. And although melanin is restricted within the relatively thin melanocytes in the Stratum basale layer (0.0006"/0.015 mm) and melanosomes in the *Stratum spinosum* layer (0.0024"/0.060 mm) of the epidermis, its presence as a variable among humans should be considered. Detailed in FIG. 27 is a comparison of high to low melanin content in the uppermost layers of human skin by way of an approximate distribution in the uppermost skin layers.

An example of the influence of melanin on optical interrogation has been seen with the wide deployment of optical pulse oximeters. Pulse oximetry utilizes two color absorption spectroscopy for signal extraction coupled with adaptive filter technology and proprietary algorithms to separate the arterial signal from nonarterial noise (venous blood movement).

When early instrument developer Hewlett-Packard Co. engaged in their endeavor in 1976, they specifically tested black and non-black subjects. Presented in T. J. Hayes and E. B. Merrick, "Continuous, Non-Invasive Measurements of Blood Oxygen Levels," Hewlett-Packard Journal, Vol. 28, no. 2, October 1976, pp. 2-10 is a set of plots in FIG. 5 revealing the greater absorption of infrared light by skin with a higher melanin content. Later in A. Matas, M. G. Sowa, G. Taylor, and H. H. Mantsch, "Melanin as a confounding factor in near infrared spectroscopy of skin." Vib. Spectrosc. 28, 45-52 (2002) this same issue was identified. And yet again with J. R. Feiner, J. W. Severinghaus, P. E. Bickler, "Dark Skin Decreases the Accuracy of Pulse Oximeters at Low Oxygen Saturation: The Effects of Oximeter Probe Type and Gender," Anesthesia & Analgesia 105(6):p S18-S23, December 2007. | DOI: 10.1213/01.ane.0000285988.35174.d9 we see instrument developers straying from the science by relying upon single algorithms to represent the full human population.

Optimization of our precision reflective sensing may include establishing a melanin concentration level in the skin under interrogation. There are two paths to achieving a measurement of this concentration represented in FIG. 28.

One path relies on measuring the colors of reflected ambient light from skin with a color camera. Such state-of-the-art cameras include the ams OSRAM TCS3530 True Color Sensor housed in a 2.5 mm×1.8 mm×1.5 mm Organic Land Grid Array (OLGA) package and the VISHAY VEML6040 red, green, blue, and white color sensor in a 2.0 mm×1.25 mm×1.0 mm surface mount package. Both small color sensing devices incorporate photodiodes, amplifiers, and analog circuits with temperature compensation operating at low voltages for power efficient operation. An actual white light emitter may be employed to generate the ambient light such that the color camera would be functional in darkness. The identified color is then compared to known melanin color levels such as that presented by the Fitzpatrick scale or others with finer gradations for adjustment to the target analyte calibration curve.

The other path utilizes a UV emitter and detector system based upon melanin having the strongest absorption in the UV region of 100 nm to 450 nm. The UV emitter interrogates the upper skin layers by absorption spectroscopy and the detector captures re-emitted UV energy to determine an absorption spectroscopic value for establishing the melanin concentration at or near the target analyte interrogation zone.

An ideal UV wavelength for this amendment calibration system is on an Isobestic point for oxygenated and deoxygenated blood absorption. At the Isobestic point, measurements are more stable. 432 nm is one such optimum Isobestic point for this optical interrogation to provide the highest accuracy of melanin content in skin.

The information derived from establishing a melanin concentration is factored into running adjustments to the main calibration curve for regular monitoring of the target analyte concentration by reflective sensing with Airware's RODI methodology and devices.

Other Factors Affecting Calibration

Two additional factors affecting calibration of a reflective optical sensor system include the age of human skin and a measurement or approximation of the thickness of the subcutaneous layer where fat can accumulate in skin. As illustrated in FIG. 29, you see the hand of a young individual that presents as having smooth skin and the hand of an aged individual exhibiting wrinkles. Wrinkles in skin result from reduced production of collagen and elastin over time as well as greater dehydration as surface skin thins over time. The more uneven the surface of skin, the more it will scatter light whereas smooth skin will more uniformly both reflect and absorb interrogating light energy that is interpreted as youthful glow. With wrinkled skin, it becomes even more imperative to establish pressure of the optical surface for the introduction of interrogating light energy directly as possible to the skin to eliminate the hills and valley effects that can cause uneven shadowing of light.

Another factor entering into management of the calibration curve of a reflective optical sensor is the thickness of adipose tissue present in the skin of the subject being optically scanned. One approximation is with the Body Mass Index (BMI).

$$BMI=Weight(kilograms)/[Height(meters)]^2$$

With a higher BMI, there is typically an increased amount of subcutaneous adipose tissue below the dermis and epidermis layers. In FIG. 30, a lower BMI condition with lower adipose fat layer is compared to a higher BMI condition with a thicker adipose fat layer. Fat has slightly different optical properties compared to the other components in human skin, absorbing and scattering light differently. Again, for precision in optical measurement of specific analytes in human skin, having a method of incorporating a BMI or other value representative of the general adipose fat layer thickness will enhance accuracy.

With both age and BMI, these values are measured externally and can be incorporated by simple data input on device setup to help manage the calibration curve under which optical measurements are converted to actual analyte concentration values.

Overall, while a higher BMI could potentially influence the way IR light interacts with the skin due to differences in adipose tissue and scattering properties, the actual impact is likely to be multifaceted and would require detailed scientific investigation to provide precise information on how it might affect the calibration process and the extent of its impact if it is not included in the calibration process.

Beyond incorporation of the electro-optics into a hand-held, easily portable instrument, one embodiment is size reduction of the entire electro-optical system into a wearable patch device. Portrayed in FIG. 31 are the top, side, and bottom views of a Reflective Sensor Patch Module. This module provides the convenience of easy carry for spot checking on the body at any number of locations, or mounting of the module to a particular body location such as the upper arm, back, stomach, or thigh where body hair would be a minimal consideration. Certain locations may lend themselves to an elastic type band to compress the module to the skin. For other locations and for extended wear times, the ideal solution is an adhesive interface. Also described in FIG. 31 is the Multi-function Adhesive Interface (MAI) that might not only serve as a mechanical attachment of the module to the skin, but can serve other functions. One critical element of the MAI will be an index of refraction matching film or fluid aligned with the emitter and detector optics. A second element of the MAI may provide electrically compatible zones serving as suitable bioimpedance interfaces to the skin's surface to provide assessment of the hydration and well-being of the skin to provide information valuable to maintaining calibration matching of the sensor to the current skin's biophysical condition. A third element of the MAI may enhance the conductive thermal interface of a temperature sensor in the module, again providing addition data on the human biophysical state for calibration management. As a point of design consideration, the thermally conductive and/or electrically conductive interfaces may include such elements as (1) Silver
(2) Gold
(3) Copper
(4) Stainless steel
(5) Conductive polymers like PEDOT:PSS (Poly(3,4-ethylenedioxythiophene) polystyrene sulfonate)
(6) Silver-plated nylon or another polymer that can be produced as a woven or non-woven matrix
(7) Carbon
(8) Carbonized rubber or silicone with or without a supporting carrier like a very thin webbing of polymer or natural material like cotton or hemp
(9) Silver powder or flake impregnated rubber or silicone Any chosen materials should serve to be non-hypoallergenic, low cost, and environmentally friendly as possible as this MAI will be a disposable item as once it is removed from the skin, the overall integrity of the MAI will be severely degraded.

While the invention described herein with reference to certain preferred embodiments, these embodiments have been presented by way of example only, and not to limit the scope of the invention. For example, while a number of factors have been identified that can affect accuracy of calibration when the concentration of the targeted molecule in the liquid sample of human skin is calculated, not all such factors need be taken into account in all circumstances, depending upon the application and amount of accuracy that may be required or useful. Also, as already mentioned, the factors identified in the present application, except for those peculiar to reflective sensing, can also be used to improve accuracy of transmissive sensing. Therefore, in view of the foregoing disclosure, additional embodiments will be obvious to those skilled in the art having the benefit of this detailed description.

Accordingly, still further changes and modifications in the actual concepts described herein can readily be made without departing from the spirit and scope of the disclosed invention.

The invention claimed is:

1. A process for quantifying a concentration of a targeted molecule in a liquid sample through use of an absorption spectroscopy process, comprising:
   (1) pulsing a signal beam with a signal pulsed source;
   (2) pulsing a reference beam with a reference pulsed source;
   (3) spatially combining the pulsed signal beam and the pulsed reference beam into a single radiation beam which passes into the liquid sample to a first effective depth and then is reflected out of the liquid sample;
   (4) detecting a pulsed signal beam output and a pulsed reference beam output after the single radiation beam passes out of the liquid sample;
   (5) processing the pulsed signal beam output and the pulsed reference beam output to obtain a value over a preselected period of time;
   (6) repeating steps (1) through (5) for at least one additional effective depth to obtain a sampling dataset; and
   (7) calculating a concentration level of the targeted particle in the liquid sample based on the sampling dataset;
   wherein the signal pulsed source emits radiation at the signal bandwidth which is coincident with an absorption band of the targeted particle while the reference pulsed source emits radiation at a reference wavelength which is not coincident with the absorption band; and
   wherein the signal pulsed source is separate from the reference pulsed source.

2. The process of claim 1, wherein a power level of the single radiation beam is adjusted for each of the plurality of variable effective depths.

3. The process of claim 1, wherein a plurality of different effective focusing depths are used to obtain a plurality of variable effective depths.

4. The process of claim 1, wherein the concentration is calculated by use of a calibration dataset obtained from use of the absorption spectroscopy process on a plurality of a samples having a known concentration of the targeted molecule.

5. The process of claim 1, wherein the concentration is calculated by use of a calibration dataset obtained from use of the absorption spectroscopy process on a sample having a known concentration of the targeted molecule using a plurality of variable identical pathlengths.

6. The process of claim 1, wherein the concentration is calculated by use of a calibration dataset for a plurality of known concentrations of the targeted molecule for a plurality of human conditions.

7. The process of claim 1, wherein a plurality of different effective focusing depths used to obtain the sampling dataset is achieved by positioning a single beam focal point lens at two or more positions with respect to a sampling surface of the liquid sample.

8. The process of claim 1, wherein a plurality of different effective focusing depths used to obtain the sampling dataset is achieved by using a variable focus lens system that employs a lens shape change mechanism to modify a focal length of the single radiation beam.

9. The process of claim 1, wherein a plurality of different effective focusing depths used to obtain the sampling dataset is achieved by swapping of a plurality of lenses, each of said plurality of lenses having a different focal length.

10. An apparatus for quantifying a concentration of a targeted molecule in a liquid sample, comprising:
a device configured to use an absorption spectroscopy process comprising the following steps:
(1) pulsing a signal beam with a signal pulsed source;
(2) pulsing a reference beam with a reference pulsed source;
(3) spatially combining the pulsed signal beam and the pulsed reference beam into a single radiation beam which passes into the liquid sample to a first effective depth and then is reflected out of the liquid sample;
(4) detecting a pulsed signal beam output and a pulsed reference beam output after the single radiation beam passes out of the liquid sample;
(5) processing the pulsed signal beam output and the pulsed reference beam output to obtain a value over a preselected period of time;
(6) repeating steps (1) through (5) for at least one additional effective depth to obtain a sampling dataset; and
(7) calculating a concentration level of the targeted particle in the liquid sample based on the sampling dataset;
wherein the signal pulsed source emits radiation at the signal bandwidth which is coincident with an absorption band of the targeted particle while the reference pulsed source emits radiation at a reference wavelength which is not coincident with the absorption band; and
wherein the signal pulsed source is separate from the reference pulsed source.

11. The apparatus of claim 10, further comprising a refractive index matching material applied to a surface through which the single radiation beam passes before it is passed into the liquid sample in the absorption spectroscopy process, said refractive index matching material being configured to enhance optical energy entering into the liquid sample.

12. The apparatus of claim 11, wherein the refractive index matching material is configured so that light energy re-emitted from the liquid sample passes through said refractive index matching material and said refractive index matching material enhances optical energy exiting from the liquid sample.

13. The apparatus of claim 12, further comprising an adhesive matrix for attaching the apparatus to a subject skin as a wearable device.

14. The apparatus of claim 13, wherein the adhesive matrix is detachable from the device.

15. The apparatus of claim 13, further comprising a temperature sensor and means for using temperature sensed by said temperature sensor in the absorption spectroscopy process to enhance overall accuracy of the calculation of the concentration level of the targeted particle in the liquid sample.

16. The apparatus of claim 15, further comprising a color sensor and means for using color sensed by said color sensor in the absorption spectroscopy process to enhance overall accuracy of the calculation of the concentration level of the targeted particle in the liquid sample.

17. The apparatus of claim 13, further comprising a color sensor and means for using color sensed by said color sensor in the absorption spectroscopy process to enhance overall accuracy of the calculation of the concentration level of the targeted particle in the liquid sample.

18. The apparatus of claim 17, further comprising means for measuring melanin when the liquid sample is in a human body and means for using melanin concentration to enhance overall accuracy of the calculation of the concentration level of the targeted particle in the liquid sample.

19. The apparatus of claim 13, further comprising means for measuring melanin when the liquid sample is in a human body and means for using melanin concentration to enhance overall accuracy of the calculation of the concentration level of the targeted particle in the liquid sample.

20. The apparatus of claim 13, further comprising means for using at least one characteristic of the subject skin to enhance overall accuracy of the calculation of the concentration level of the targeted particle in the liquid sample.

* * * * *